(12) United States Patent
Doddroe et al.

(10) Patent No.: US 7,833,287 B2
(45) Date of Patent: *Nov. 16, 2010

(54) ADJUSTABLE MULTI-AXIS PROSTHETIC ANKLE AND METHOD OF USE THEREOF

(75) Inventors: Jeffrey L. Doddroe, Washington Court House, OH (US); Lonnie L. Nolt, Washington Court House, OH (US)

(73) Assignee: The Ohio Willow Wood Company, Mount Sterling, OH (US)

( * ) Notice: Subject to any disclaimer, the term of this patent is extended or adjusted under 35 U.S.C. 154(b) by 693 days.

This patent is subject to a terminal disclaimer.

(21) Appl. No.: 11/613,843

(22) Filed: Dec. 20, 2006

(65) Prior Publication Data

US 2007/0106396 A1 May 10, 2007

Related U.S. Application Data

(63) Continuation-in-part of application No. 11/421,595, filed on Jun. 1, 2006, now Pat. No. 7,563,288, which is a continuation-in-part of application No. 10/770,833, filed on Feb. 3, 2004, now Pat. No. 7,112,227, which is a continuation-in-part of application No. 09/893,887, filed on Jun. 29, 2001, now Pat. No. 6,699,295.

(51) Int. Cl.
*A61F 2/66* (2006.01)
*A61F 2/64* (2006.01)

(52) U.S. Cl. .......................................... 623/49; 623/47

(58) Field of Classification Search .............. 623/47–55
See application file for complete search history.

(56) References Cited

U.S. PATENT DOCUMENTS

| | | | |
|---|---|---|---|
| 3,956,775 A * | 5/1976 | Moore ......................... 623/50 |
| 3,982,280 A * | 9/1976 | Asbelle et al. ................ 623/49 |
| 4,089,072 A | 5/1978 | Glabiszewski | |
| 4,395,783 A * | 8/1983 | Eyre et al. .................... 623/47 |
| 4,461,045 A | 7/1984 | Shorter et al. | |
| 4,463,459 A | 8/1984 | Shorter et al. | |
| 4,645,508 A | 2/1987 | Shorter et al. | |
| 4,792,340 A | 12/1988 | Aulie et al. | |
| 5,008,563 A * | 4/1991 | Kenney et al. .............. 327/176 |

(Continued)

FOREIGN PATENT DOCUMENTS

DE 102005004794 9/2005

(Continued)

*Primary Examiner*—William H Matthews
*Assistant Examiner*—Marcia Hoffman
(74) *Attorney, Agent, or Firm*—Standley Law Group LLP

(57) ABSTRACT

A multi-axis prosthetic ankle having an adjustable range of articulation and a method of adjusting the range of articulation of such an ankle. A lower leg connection component extends from the receiving cavity of a prosthetic foot connection component. The remainder of the receiving cavity is substantially filled with an elastomeric material. An interchangeable external bearing resides atop a portion of the elastomeric material and includes an aperture through which a portion of the lower leg connection component passes. By exchanging an installed external bearing for an external bearing having an aperture of different size, the limits of movement of the lower leg connection component can be altered and the overall range of articulation of the ankle adjusted.

20 Claims, 21 Drawing Sheets

Section F-F

U.S. PATENT DOCUMENTS

| | | |
|---|---|---|
| 5,019,109 A | 5/1991 | Voisin |
| 5,112,356 A | 5/1992 | Harris et al. |
| 5,116,383 A | 5/1992 | Shorter et al. |
| 5,156,630 A | 10/1992 | Rappoport et al. |
| 5,314,499 A | 5/1994 | Collier |
| 5,376,139 A | 12/1994 | Pitkin |
| 5,405,410 A * | 4/1995 | Arbogast et al. ............... 623/47 |
| 5,443,527 A | 8/1995 | Wilson |
| 5,545,234 A | 8/1996 | Collier |
| 5,571,212 A | 11/1996 | Cornelius |
| 5,766,264 A | 6/1998 | Lundt |
| 5,769,896 A * | 6/1998 | Rosendahl et al. ............ 623/49 |
| 5,800,568 A | 9/1998 | Atkinson et al. |
| 6,120,547 A * | 9/2000 | Christensen ................. 623/52 |
| 6,387,134 B1 | 5/2002 | Parker et al. |
| 6,666,895 B2 | 12/2003 | Johnson et al. |
| 6,699,295 B2 | 3/2004 | Lee et al. |
| 6,811,571 B1 | 11/2004 | Phillips |
| 6,855,170 B2 | 2/2005 | Gramnas |
| 7,112,227 B2 | 9/2006 | Doddroe et al. |
| 2004/0236436 A1 | 11/2004 | Draghetti |
| 2005/0060045 A1 | 3/2005 | Smith et al. |
| 2005/0109563 A1 | 5/2005 | Vitale et al. |

FOREIGN PATENT DOCUMENTS

| | | |
|---|---|---|
| FR | 2653327 | 10/1992 |
| GB | 2410692 | 8/2005 |
| JP | 6225898 | 8/1994 |
| JP | 984814 | 1/1997 |
| JP | 11345 | 3/1999 |
| WO | 0076429 A1 | 12/2000 |
| WO | 03086245 A2 | 10/2003 |

\* cited by examiner

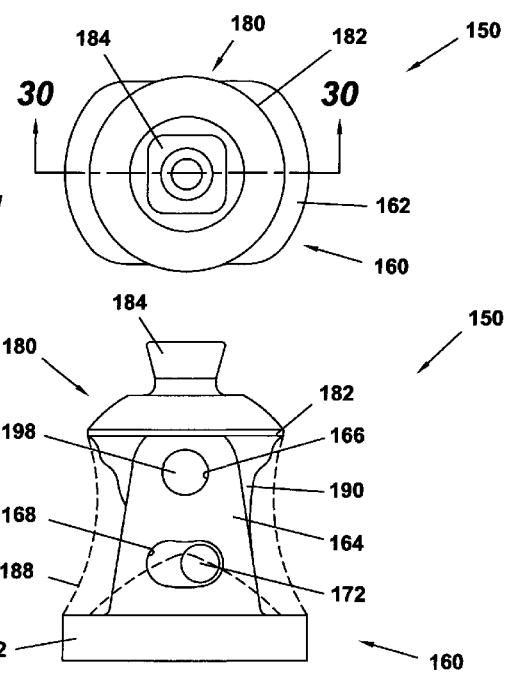
FIG. 21
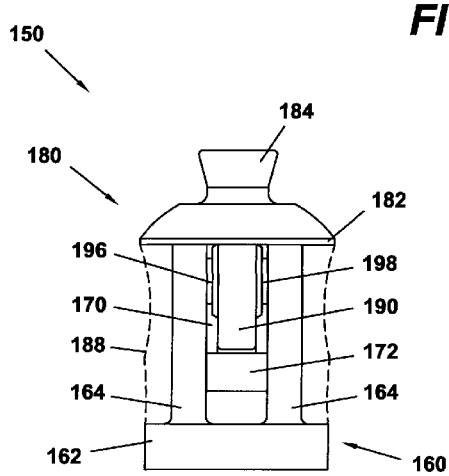
FIG. 22
FIG. 23

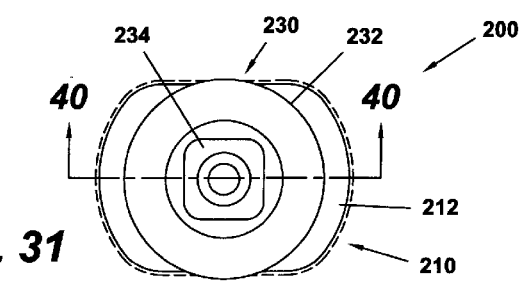
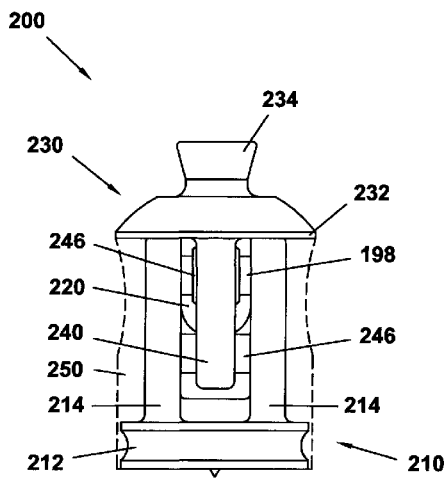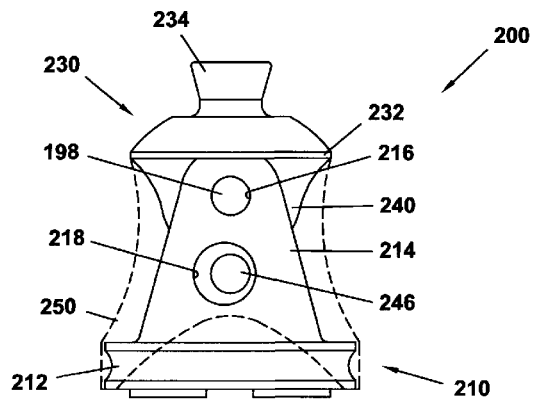
FIG. 31
FIG. 32
FIG. 33

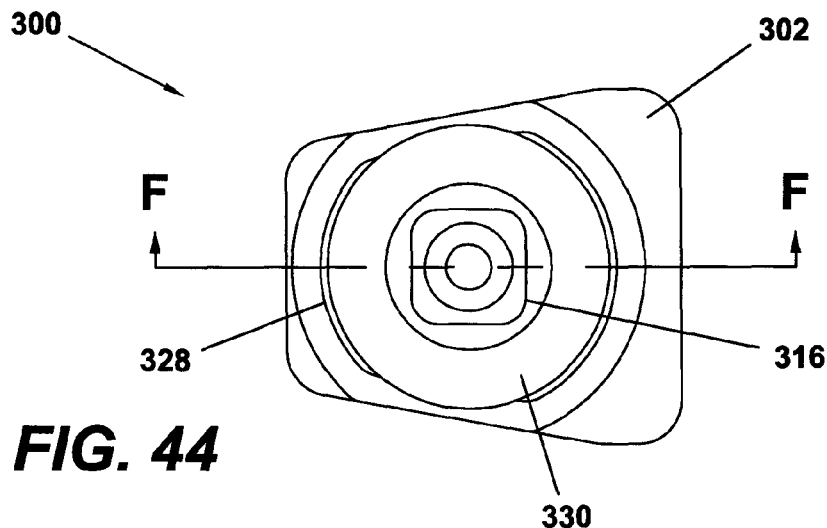
FIG. 44
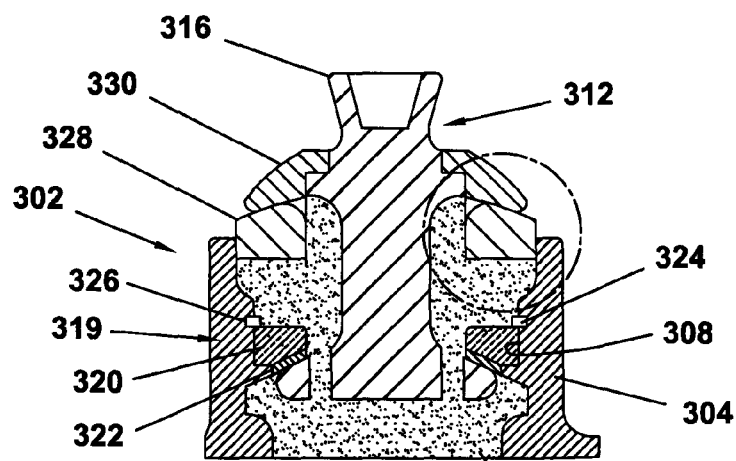
FIG. 45    Section F-F
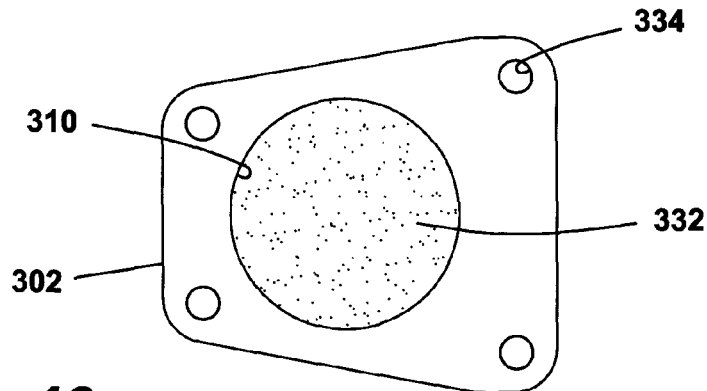
FIG. 46

DETAIL A

DETAIL B

DETAIL C

ADJUSTABLE MULTI-AXIS PROSTHETIC ANKLE AND METHOD OF USE THEREOF

This application is a continuation-in-part of U.S. patent application Ser. No. 11/421,595, filed on Jun. 1, 2006, now U.S. Pat. No. 7,563,288, which is a continuation-in-part of U.S. patent application Ser. No. 10/770,833, filed on Feb. 3, 2004, now U.S. Pat. No. 7,112,227, which is a continuation-in-part of U.S. patent application Ser. No. 09/893,887, filed on Jun. 29, 2001, now U.S. Pat. No. 6,699,295.

BACKGROUND

The present invention relates generally to prosthetic devices, and more particularly to multi-axis prosthetic ankles.

A prosthetic ankle is a component which connects a prosthetic foot with a prosthetic lower leg. For smooth walking, especially, across uneven ground, it is important for the ankle to be designed for a full range of foot motion with respect to the lower leg prosthesis. One embodiment of such an ankle is described in U.S. patent application Ser. No. 09/893,887, which is hereby incorporated by reference herein. Most prosthetic ankles currently on the market, however, do not provide optimally controlled multi-axis motion. Often the prosthetic ankle has such a low stiffness that it effectively reduces any functional capabilities of the attached prosthetic foot, resulting in a choppy, unnatural and uncomfortable gait. Some ankles require adjustments to the assembly in order to achieve the desired function.

A full range of motion may be accomplished by the use of multiple axes of rotation in the ankle joint. However, conventional prosthetic ankle joints that provide multi-axis motion tend to require extensive maintenance including the replacement of parts in order to function properly. This is because the conventional ankle joint designs require elastic members to slide in contact with either a rigid surface, which is typically metallic, or another elastic surface. This surface-to-surface sliding motion is the primary cause of material breakdown.

SUMMARY OF EXEMPLARY EMBODIMENTS

It is therefore an object of the present invention to provide a multi-axis prosthetic ankle joint which does not suffer from the shortcomings of the prior art.

One embodiment of a multi-axis prosthetic ankle joint of the present invention includes a bottom component adapted to be connected to a prosthetic foot, a lower leg connection component adapted to be connected to a prosthetic lower leg, an elastomeric material securely connecting the bottom component with the lower leg connection component, and a mechanical device suspended in the elastomeric material. In this embodiment, the mechanical device comprises a first rigid element connected to the bottom component but not to the lower leg connection component, and a second rigid element connected to the lower leg connection component but not to the bottom component. The first and second elements interlockingly float in the elastomeric material, and are not in direct contact with one another, so as to permit relative movement of the bottom component and the lower leg connection component by deformation of the elastomeric material.

In this particular embodiment of the present invention, the mechanical device comprises a generally U-shaped first part connected to the bottom component so as to define a first aperture, and a generally U-shaped second part connected to the lower leg connection component so as to define a second aperture. The first part floatingly extends through the second aperture, and the second part floatingly extends through the first aperture.

An alternate embodiment of a multi-axis prosthetic ankle of the present invention may also include a bottom, prosthetic foot connection component adapted to be connected to a prosthetic foot, a lower leg connection component adapted to be connected to a prosthetic lower leg, an elastomeric material securely connecting the prosthetic foot connection component with the lower leg connection component, and a mechanical device suspended in the elastomeric material. In this embodiment, the mechanical device comprises a first rigid element in the prosthetic foot connection component that is not connected to the lower leg connection component, and a second rigid element connected to the lower leg connection component but not to the prosthetic foot connection component. The position of the first and second elements is maintained by the elastomeric material. The first element may act as a stop for restricting the range of motion of the lower leg connection component, but otherwise the first and second elements are not in direct contact with one another. As such, relative movement of the prosthetic foot connection component and the lower leg connection component occurs through deformation of the elastomeric material.

In this particular embodiment of the present invention, the mechanical device comprises a cavity in the prosthetic foot connection component that is substantially defined by a plurality of vertically extending walls, and a generally hook-shaped projection extending from the lower leg connection component. The hook-shaped projection of the lower leg connection component floatingly resides within the cavity in the prosthetic foot connection component. Contact between a portion of the hook-shaped projection and a rigid wall of the prosthetic foot connection component can be utilized to restrict the range of motion of the lower leg connection component. Other points of contact between the lower leg connection component and the prosthetic foot connection component may be similarly utilized.

By terms such as "interlockingly float" and "floatingly resides" it is meant that the first and second elements are suspended in the elastomeric material in close relation to one another, but are retained in position by the intermediary elastomeric material, not by contact with one another. Since the deformation of the elastic material permits multi-axis relative movement of the bottom component and the lower leg connection component, including translational movement, the ankle joint of the invention can simulate natural ankle motion by providing plantar flexion, dorsi flexion, inversion, eversion, translation and internal/external rotational movement. Such motion is optimally controlled by the multi-axis deformation of the elastic material, without sacrificing the energy return of the prosthetic foot. Further, since the components of the mechanical device are bonded to, and encased by, the elastomeric material, the ankle has the ability to absorb and damp both rotational and linear impacts.

As force is applied to either of these ankles, the ankle moves in rotation and translation with a fluid motion by deforming the elastomeric medium. According to a further feature of the invention, at least one mechanical stop may also be positioned on/in either of these multi-axis ankle embodiments to prevent the relative angular movement of the ankles from deforming the elastomeric material beyond the elastic limit thereof. Since the deformation of the elastomeric material in both multi-axis ankle embodiments is thus always kept within the elastic limit, any tendency toward breakdown of the elastomeric material is further reduced.

In another embodiment of a multi-axis prosthetic ankle of the present invention, the ankle may include a bottom, prosthetic foot connection component adapted to be connected to a prosthetic foot, a lower leg connection component adapted to be connected to a prosthetic lower leg, an elastomeric material residing between the prosthetic foot connection component and the lower leg connection component, and a mechanical connection suspended in the elastomeric material. In this embodiment, the prosthetic foot connection component and the lower leg connection component are mechanically coupled and are preferably substantially encased within the elastomeric material. A portion of the prosthetic foot connection component may act as a stop for restricting the range of motion of the lower leg connection component. Unlike the previously described exemplary embodiments, this multi-axis ankle embodiment does not rely solely on the elastomeric material to maintain the positional relationship between the prosthetic foot connection component and the lower leg connection component. Consequently, in this exemplary embodiment of the present invention, relative movement of the prosthetic foot connection component and the lower leg connection component occurs through deformation of the elastomeric material as well as through the mechanical connection.

In this particular embodiment of the present invention, the mechanical connection may comprise a pin that resides in an aperture passing through both an upwardly-extending portion of the prosthetic foot connection component and a downwardly-extending projection of the lower leg connection component. A bearing, such as a spherical bearing, may be located in the downwardly-extending projection of the lower leg connection component to receive the pin and enhance movement of the lower leg connection component. The upwardly-extending portion of the prosthetic foot connection component may comprise two legs, such that the downwardly-extending projection of the lower leg connection component may reside therebetween. A dorsi-flexion stop may be located in the prosthetic foot connection component so as to contact a portion of the downwardly-extending projection of the lower leg connection component and limit the range of motion thereof. Alternatively, a dorsi-flexion stop may be located in a projection of the lower leg connection component and adapted to contact a portion of the prosthetic foot connection component in order to limit ankle movement.

As force is applied to this embodiment of the multi-axis ankle, the ankle moves in rotation with a fluid motion by pivoting about the pin and simultaneously deforming the elastomeric material. The ankle is also able to move in translation via the inherent tilting ability of the spherical bearing. Since deformation of the elastomeric material in this embodiment is always kept within the elastic limit by means of the dorsi-flexion stop and the limited translational movement of the downwardly-extending projection of the lower leg connection component, breakdown of the elastomeric material is minimized.

Since there is no surface-to-surface sliding motion within any of the aforementioned multi-axis prosthetic ankle embodiments, the material breakdown which might otherwise occur due to friction therebetween is reduced or eliminated.

According to yet a another embodiment of the present invention, a multi-axis prosthetic ankle may simply comprise a bottom component adapted to be connected to a prosthetic foot, a lower leg connection component adapted to be connected to a prosthetic lower leg, an elastomeric material securely connecting the bottom component with the lower leg connection component, and mechanical means for limiting a deformation of the elastic material.

In still another embodiment of the present invention, a multi-axis prosthetic ankle may comprise a bottom component adapted to be connected to a prosthetic foot, a lower leg connection component adapted to be connected to a prosthetic lower leg, and an elastomeric material securely connecting the bottom component with the lower leg connection component. In such an embodiment, deformation of the elastic material generally determines the range of motion of the ankle.

In another alternative embodiment of the present invention, a multi-axis prosthetic ankle may comprise a bottom component adapted to be connected to a prosthetic foot, a lower leg connection component adapted to be connected to a prosthetic lower leg, and an elastomeric material residing between the bottom component and the lower leg connection component. In this embodiment, at least one mechanical retainer is provided to retain (or help retain) the lower leg connection component in the bottom component.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIG. 21 is a top plan view of another exemplary embodiment of a multi-axis prosthetic ankle of the present invention;

FIG. 22 is a front elevation view of the multi-axis prosthetic ankle of FIG. 21, wherein an elastomeric encasing material is shown in phantom lines for purposes of clarity;

FIG. 23 is a side elevation view of the multi-axis prosthetic ankle of FIG. 21, wherein the elastomeric encasing material is again shown in phantom lines for purposes of clarity;

FIG. 31 is a top plan view of yet another exemplary embodiment of a multi-axis prosthetic ankle of the present invention;

FIG. 32 is a front elevation view of the multi-axis prosthetic ankle of FIG. 31, wherein an elastomeric encasing material is shown in phantom lines for purposes of clarity;

FIG. 33 is a side elevation view of the multi-axis prosthetic ankle of FIG. 31, wherein the elastomeric encasing material is again shown in phantom lines for purposes of clarity;

FIG. 44 is a top plan view of the multi-axis prosthetic ankle of FIG. 42;

FIG. 45 is a sectional side elevation view of the multi-axis prosthetic ankle of FIG. 42, taken along lines F-F thereof; and FIG. 46 is a bottom plan view of the multi-axis prosthetic ankle of FIG. 42.

DETAILED DESCRIPTION OF THE EXEMPLARY EMBODIMENT(S)

Figure 1:
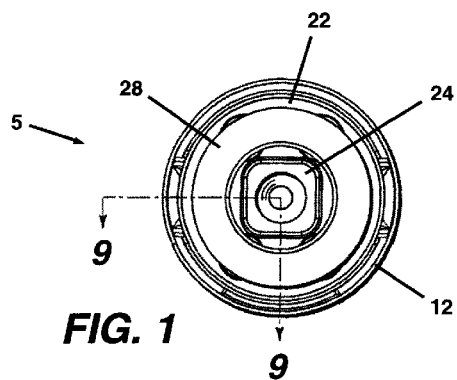
FIG. 1 is a top plan view of an exemplary embodiment of a multi-axis prosthetic ankle of the present invention.

A first exemplary embodiment of a multi-axis prosthetic ankle according to the present invention can be observed by reference to FIGS. 1-9. As can be seen, particularly with respect to FIGS. 2-3, for clarity of illustration the elastomeric casing is shown in phantom lines, thereby revealing the encased components of the mechanical device (rigid mechanical means). In this particular embodiment, the main components of the multi-axis prosthetic ankle 5 are the bottom component 10, the lower leg connection component 20, the mechanical device 30 (rigid mechanical means), and the elastomeric casing 40, which is bonded to the bottom component and the lower leg connection component and floatingly encases the elements of the mechanical device.

Figure 7:
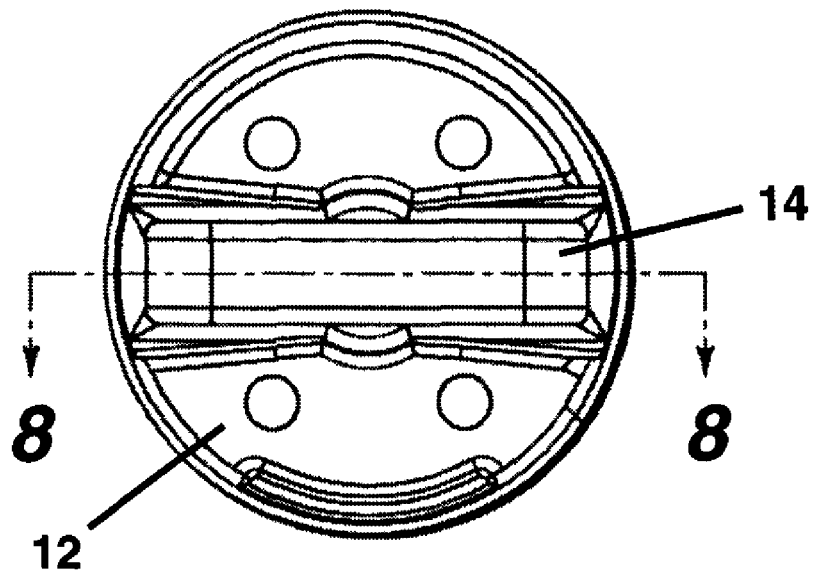
FIG. 7 is a top plan view of a bottom component of the multi-axis prosthetic ankle of FIG. 1.
Figure 8:
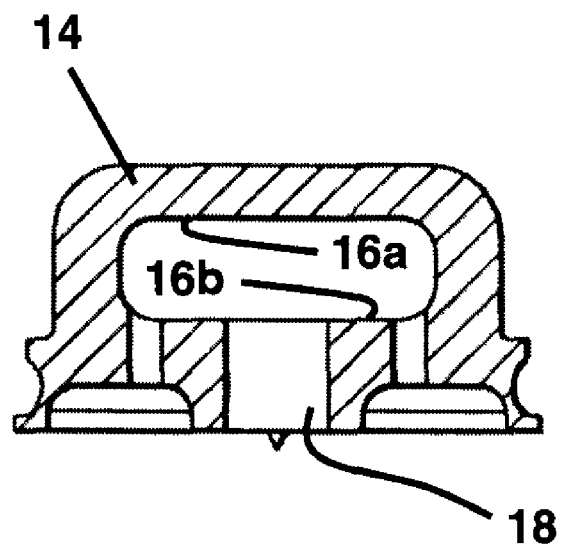
FIG. 8 is a sectional front elevation view of the multi-axis prosthetic ankle of FIG. 1, taken along lines A-A of FIG. 7.
Figure 9:
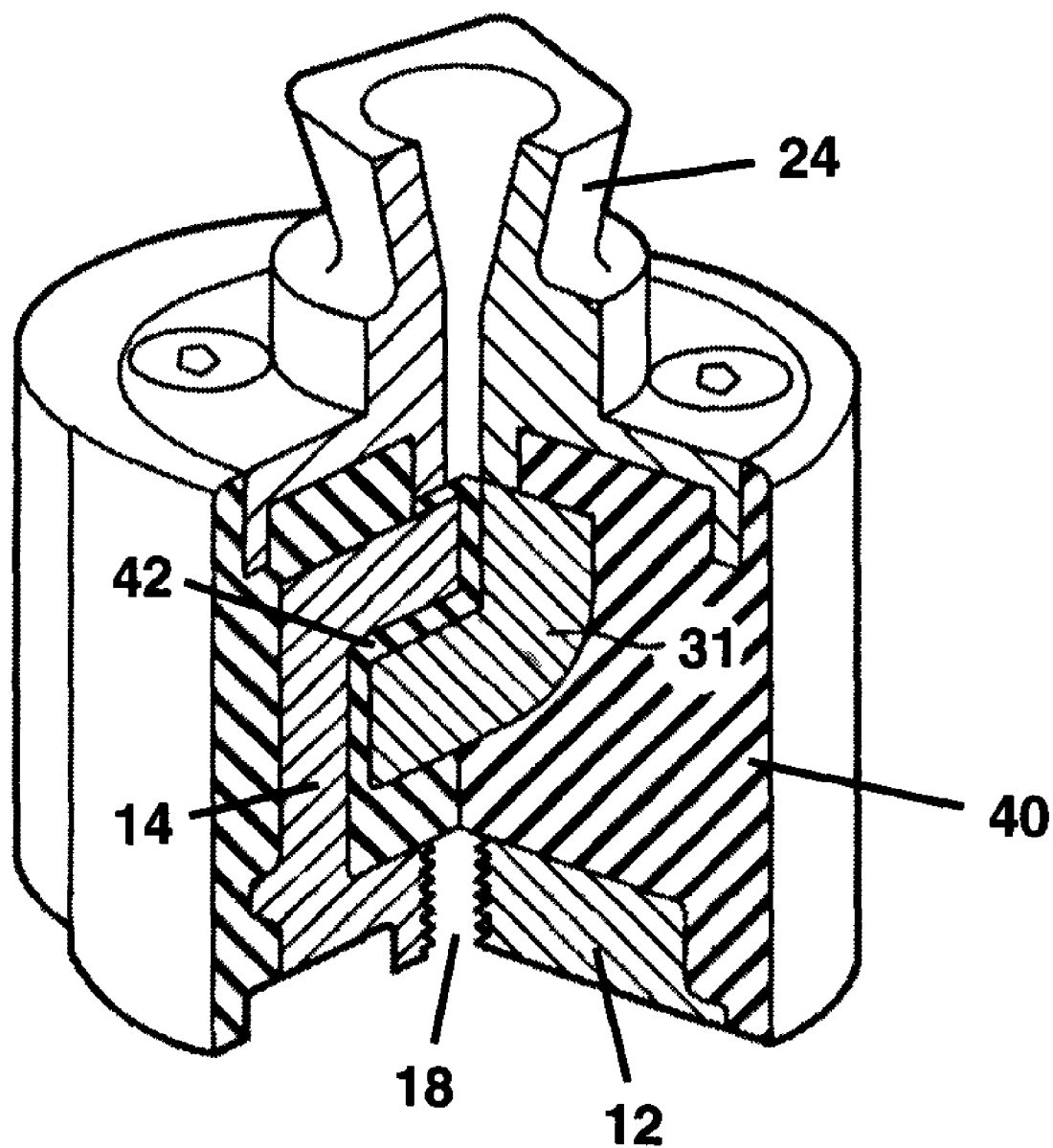
FIG. 9 is a sectional isometric view of the multi-axis prosthetic ankle of FIG. 1, taken along lines B-B of FIG. 1.
Figure 10:
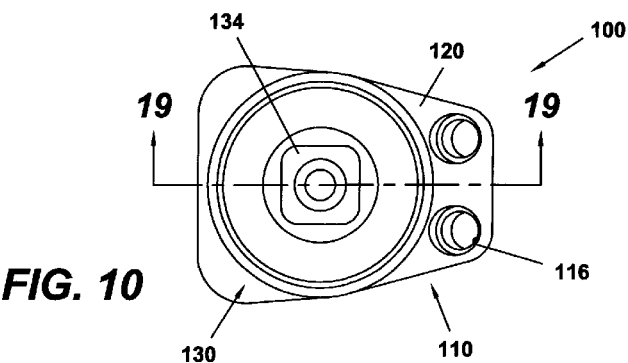
FIG. 10 is a top plan view of an alternate exemplary embodiment of a multi-axis prosthetic ankle of the present invention, wherein an elastomeric encasing material is shown in phantom lines for purposes of clarity.
Figure 11:
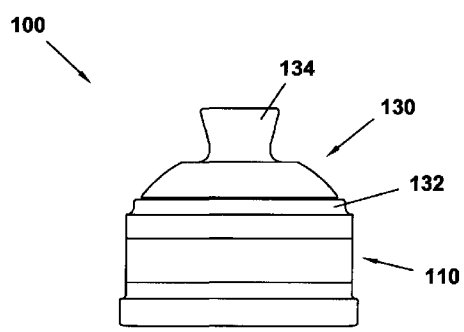
FIG. 11 is a front elevation view of the multi-axis prosthetic ankle of FIG. 10, wherein the elastomeric encasing material is again shown in phantom lines for purposes of clarity.
Figure 12:
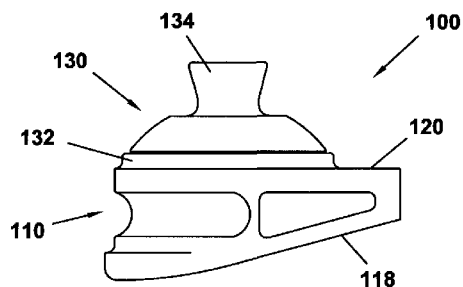
FIG. 12 is a side elevation view of the multi-axis prosthetic ankle of FIG. 10, wherein the elastomeric encasing material is again shown in phantom lines for purposes of clarity.
Figure 13:
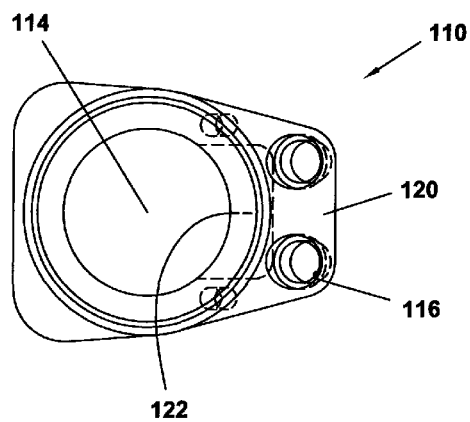
FIG. 13 is a top plan view of a prosthetic foot connection component of the multi-axis prosthetic ankle of FIG. 10.
Figure 14:
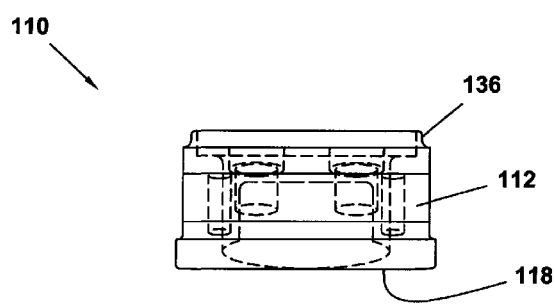
FIG. 14 is a front elevation view of the prosthetic foot connection component of FIG. 13.
Figure 15:
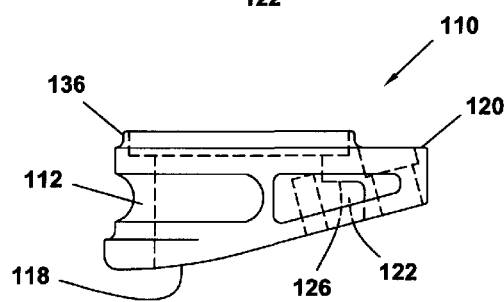
FIG. 15 is a side elevation view of the prosthetic foot connection component of FIG. 13.
Figure 16:
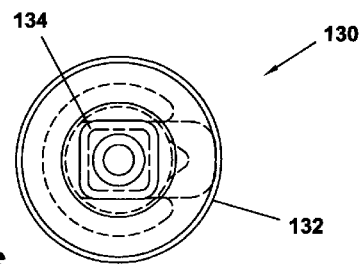
FIG. 16 is a top plan view of a lower leg connection component of the multi-axis prosthetic ankle of FIG. 10.
Figure 17:
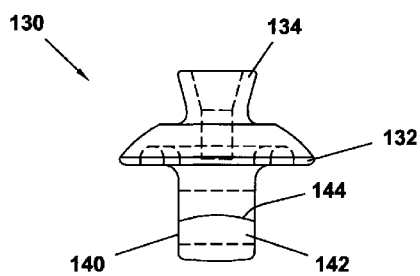
FIG. 17 is a front elevation view of the lower leg connection component of FIG. 16.
Figure 18:
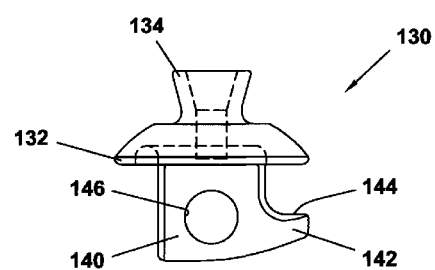
FIG. 18 is a side elevation view of the lower leg connection component of FIG. 16.

Referring more particularly to FIGS. 7 and 8, the bottom component 10 comprises a generally circular disk like base 12, and a first "U" shaped bracket 14 (first rigid element) projecting perpendicularly upwardly from the base. The first bracket 14 extends generally diametrically on the base and defines a slot like first aperture 16 having respective top and bottom surfaces 16*a* and 16*b*. The base 12 and first bracket 14 are preferably integrally formed from a rigid material such as stainless steel, but could be formed of any other rigid material such as titanium, aluminum or rigid plastic, for example. The base 12 preferably includes a threaded center hole 18 to accept a bolt or similar fastener for the securement of the bottom component 10 to a prosthetic foot.

The lower leg connection component 20 also has a generally circular disk like base 22, and has a pyramid part 24 projecting perpendicularly upward from a central portion of the upper surface of the base 22 for connection of the ankle joint to a lower leg prosthesis. The pyramid part 24 may be of a generally conventional design. The lower leg connection component 20 is also preferably integrally formed of stainless steel, but can also be formed of other rigid materials including titanium, aluminum or rigid plastic. A lower portion 26 of the pyramid part 24 may be circular to accept a separate aluminum snap on dome 28.

A second bracket 31 (second rigid element) is mounted to the lower surface of the base 22, for example by bolts 32 passing through bolt holes 34 in the base 22 and the legs of the second bracket. The second bracket 31 is also "U" shaped to define a slot like second aperture 36 having, when mounted to the base 22, respective top and bottom surfaces 36*a* and 36*b*. Moreover, a shim 38 may be positioned between one leg of the bracket 31 and the bottom of the base 22, as will be explained below. To this end, one of the legs 31*a* a of the second bracket 31 may be shorter than the other. The second bracket 31 is preferably formed of aluminum alloy, but can be formed of other rigid materials, including stainless steel, titanium or a hard plastic, for example.

Figure 2:
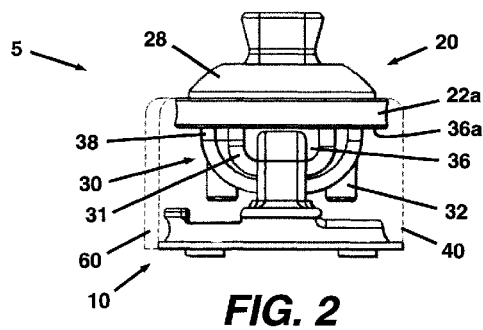
FIG. 2 is a front elevation view of the multi-axis prosthetic ankle of FIG. 1, wherein an elastomeric encasing material is shown in phantom lines for purposes of clarity.
Figure 3:
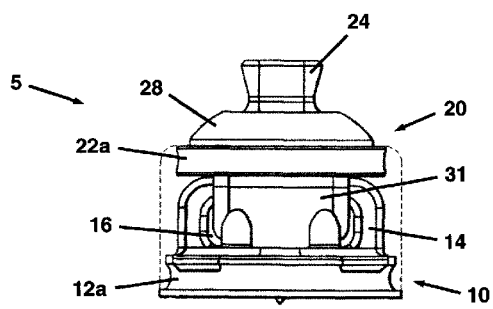
FIG. 3 is a side elevation view of the multi-axis prosthetic ankle of FIG. 1, wherein the elastomeric encasing material is again shown in phantom lines for purposes of clarity.
Figure 4:
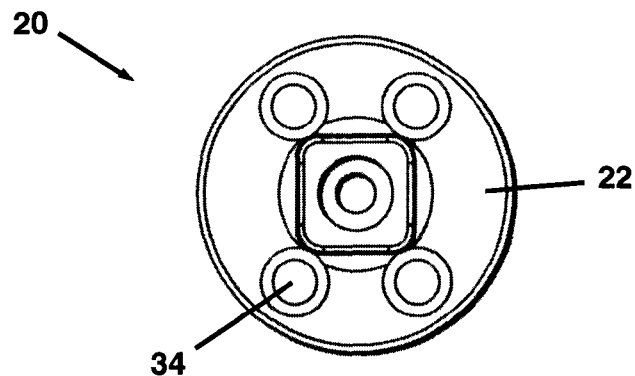
FIG. 4 is a top plan view of a lower leg connection component of the multi-axis prosthetic ankle of FIG. 1.
Figure 5:
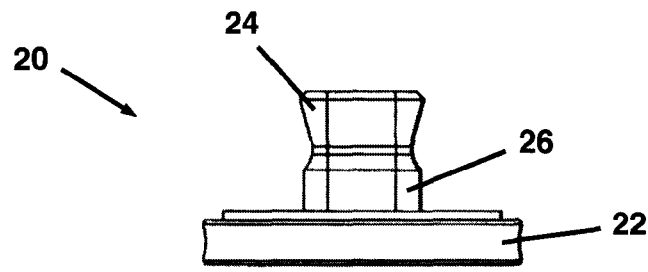
FIG. 5 is a front elevation view of the lower leg connection component of FIG. 4.
Figure 6:
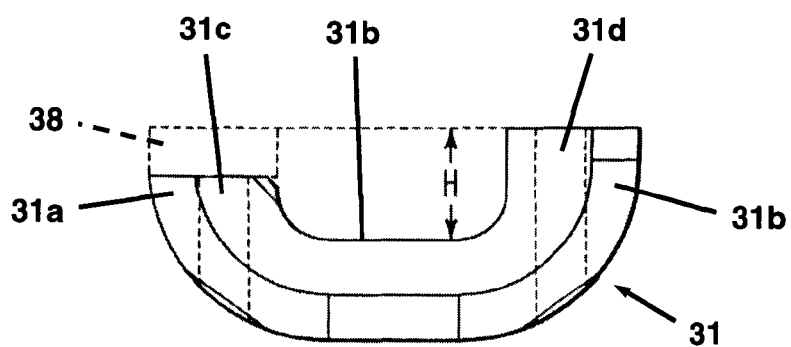
FIG. 6 is a front elevation view of a bracket for mounting to the lower leg connection component of FIGS. 4-5.

During assembly of the multi-axis prosthetic ankle, the second bracket 31 is interlockingly positioned within the slot like aperture 16 of the first bracket 14 to form the mechanical device 30, after which the second bracket 31 is bolted to the lower surface of the base 22 of the lower leg connection component 20 via the bolts 32 and the optional shim 38. At this time, a shim 38 of a proper thickness is selected on the basis described below, and is positioned between the end of the shorter one of the legs of the second bracket 31 and the lower surface of the base 22. As will be readily understood by those skilled in the art, the shim has a through hole for the bolt 32, and the legs 31a and 31b of the second bracket 31 have respective threaded through holes 31c and 31d. The resulting assembly is generally shown in FIGS. 1-3.

Subsequently, the assembly of the bottom component 10, lower leg connection component 20 and the second bracket 31 is placed within a mold (not shown). At this time, the assembly of the lower leg connection component 20 and second bracket 31 is held in a slightly elevated position so that the surfaces 36a and 36b of the second aperture 36 do not contact either of the surfaces 16a or 16b of the first bracket 14. Instead, the second bracket 31 is held so as to float without contact with the first bracket 14. While the ankle components are held in this position, an elastomeric material in a flowable state is injected or otherwise introduced into the mold and permitted to harden. The elastomeric material is preferably a rubber, and more preferably a thermoset rubber polymer having a high resistance and memory under cyclical loading. Non-limiting examples include butyl rubber, ethylene-propylene rubber, neoprene rubber, nitrile rubber, polybutadiene rubber, polyisoprene rubber, stereo rubber, styrene-butadiene rubber, natural rubber, or a combination of two or more of these rubbers.

The elastomeric material thereby encases and bonds to the bottom component 10, the lower leg connection component 20 and the mechanical device 30 composed of the interlocking brackets 14 and 31. The rigid components are thus fused together with the elastomeric material to form a flexible assembly. This allows for a smooth transition through the entire gait cycle of a user of the ankle, from heel strike, through midstance, to toe off. As can be seen from FIG. 9, the interlocking brackets 14 and 31 do not contact one another but instead are floatingly bonded through the intermediary of an intervening portion 42 of the elastomeric material casing 40. The peripheral surfaces of the bases 12, 22 of the bottom component 10 and the lower leg connection component 20, respectively, may have annular concave recesses 12a, 22a at their circumferential peripheries. These annular recesses improve the grip of the rubber material bonded to the components 10, 20.

Once the above-described assembly and molding process is accomplished, the snap on dome 28 may be optionally mounted to the pyramid part 24. The completed multi-axis ankle assembly 5 can then be incorporated into a lower leg prosthesis in a conventional manner.

The elastomeric casing 40 may optionally include a protruding enlargement 60 at the posterior part of the ankle 5. The protruding enlargement 60 acts as a tendon and serves to stiffen the ankle 5 when the toe of an attached prosthetic foot is loaded.

By selecting a shim 38 of the proper thickness, one can control the thickness of the elastomeric material 42 in the spaces which separate the first and second brackets 14, 31. One can thereby control the compliance of the joint depending upon the expected loads, which can be anticipated by the weight and general physical activity level of the intended user. This done by selecting a shim 38 (or shims) of a thickness that will provide a desired height "H" for the aperture 36, which allows for a predetermined spacing between the brackets 14, 31, and by the selection of the hardness of the elastomeric casing material 40. A shore hardness A of between 70 and 99 is typically selected for adults, whereas a shore hardness A of between 50 and 70 is typically selected for children. For easy reference, the snap on dome 28 can be color coded to the rubber hardness.

The angular degree of rotational motion between the bottom component 10 and the lower leg connection component 20 is preferably limited by stops. In one embodiment, the stops take the form of a limit of the compression of the elastomeric material 40 that is caused by the turning of the interlocking brackets 14, 31. That is, by selecting a proper shim to provide a desired height "H" for the aperture 36, one also selects the resulting thickness of the elastomeric material present between the brackets, (e.g., the intervening elastomeric material 42). As the ankle 5 pivots during ambulation, the rigid surfaces of the brackets 14, 31 approach one another while compressing the intervening elastomeric casing material. The resistance of the elastomeric material to further compression increases as the ankle pivots. When this resistance equals the turning load on the ankle, the elastomeric material acts as a fixed stop against further rotation. Since the expected load on the ankle and the compression resistance of the elastomeric material are known, one skilled in the art can select a shim for a desired height "H" to permit a predetermined rotation stop for the ankle. Of course, other forms of the rigid stops could instead be used.

The ankle 5 according to this embodiment of the present invention has a higher load range of increasing moment of resistance compared to prior art ankles, which flatten out over lower load ranges. Preferable limits of movement permitted by the stops of this particular embodiment of the ankle 5 are as follows:

Internal/External rotation: 15°/15° (300 total).
Plantar flexion: 15°.
Dorsi flexion: 15°.
Inversion/Eversion: 10°/10° (200 total).
Anterior/Posterior translation: ±0.10 to 0.375 inches.
Medial/Lateral translation: ±0.05 to 0.250 inches.
Vertical displacement: 0.030 to 0.375 inches.

It should be understood that the above limits of movement have been provided for purposes of illustration only, and the ankle 5 to which the limits apply can be designed to have other limits of movement as well.

An alternate embodiment of a multi-axis prosthetic ankle 100 of the present invention is depicted in FIGS. 10-20. This particular embodiment of the multi-axis prosthetic ankle 100 is well suited to use with a low-profile prosthetic foot, such as a prosthetic foot that may be used by an amputee having a long residual limb.

The multi-axis prosthetic ankle 100 can be seen to include a bottom, prosthetic foot connection component 110, that is adapted for attachment to a prosthetic foot, and a lower leg connection component 130 that is adapted to attach the ankle to another prosthetic leg component.

The prosthetic foot connection component 110 is essentially a box-like structure having rigid vertical walls 112 that bound a receiving cavity 114. Although not shown in the drawing figures, the prosthetic foot connection component 110 may also have a bottom wall. Threaded or unthreaded bores 116 may also be provided through the prosthetic foot connection component 110 to facilitate its attachment to a prosthetic foot. A bottom surface 118 of the prosthetic foot connection component 110 may be angled to allow for connection of the prosthetic foot connection component to a like-angled portion of a prosthetic foot, while simultaneously maintaining a top surface 120 of the prosthetic foot connection component in a substantially level position. The prosthetic foot connection component 110 may be integrally formed of titanium, but can also be formed or machined from other rigid materials, including stainless steel, aluminum, or rigid plastic, for example.

The receiving cavity 114 of the prosthetic foot connection component 110 is designed to receive the connecting projection 140 of the lower leg connection component 130. More specifically, the receiving cavity 114 of the prosthetic foot connection component 110 is designed to allow a connecting projection 140 of the lower leg connection component 130 to floatingly reside therein when the two components are properly assembled. As will be explained in more detail below, this design allows the positional relationship between the prosthetic foot connection component 110 and the lower leg connection component 130 to be maintained by an elastomeric material, as opposed to a direct mechanical connection between the two components. During ambulation of the user, the connecting projection 140 is able to move within the receiving cavity 114, allowing for flexion of the ankle 100.

This particular embodiment of the lower leg connection component 130 is shown to have a generally circular, disk-like base 132, although other shapes are also possible. A pyramid part 134 may be affixed/integral to the base and may project upward from a central dome-like portion thereof. The pyramid part 134 can be used to connect the ankle 100 to another prosthetic leg component. The pyramid part 134 may be of a generally conventional design.

Extending downward from the base 132 of the lower leg connection component 130 is a connecting projection 140. The connecting projection 140 is provided to secure the lower leg connection component 130 within an elastomeric material. The connecting projection 140 is also a rigid component, and is firmly affixed to the base 132. Preferably, the connecting projection 140 is integrally formed with the base 132, such as by molding or machining. In this particular embodiment of the ankle 100, the connecting projection 140 is shown to have a body that is generally rectangular in shape, except for a protrusion 142 extending therefrom. Although the protrusion 142 is shown to substantially form a hook shape when combined with the remainder of the connecting projection 140 body, other shapes are also possible. The connecting projection 140 is also shown to have a thickness that is significantly less than the diameter of the base 132. Of course, other shapes and thicknesses are also possible. The protrusion 142 extends laterally outward from one side of the connecting projection 140, such that a ledge 144 is formed. When assembled, the protrusion 142 is directed toward the posterior of the ankle 100. The connecting projection 140 may also have an aperture 146 passing therethrough, or partially therethrough. The aperture 146 provides for increased retention of the connecting projection 140 by the elastomeric material that will eventually surround much of the ankle components.

The lower leg connection component 130 is also preferably integrally formed of titanium, but can also be formed or machined from other rigid materials, including, stainless steel, aluminum, or rigid plastic, for example.

Figure 30:
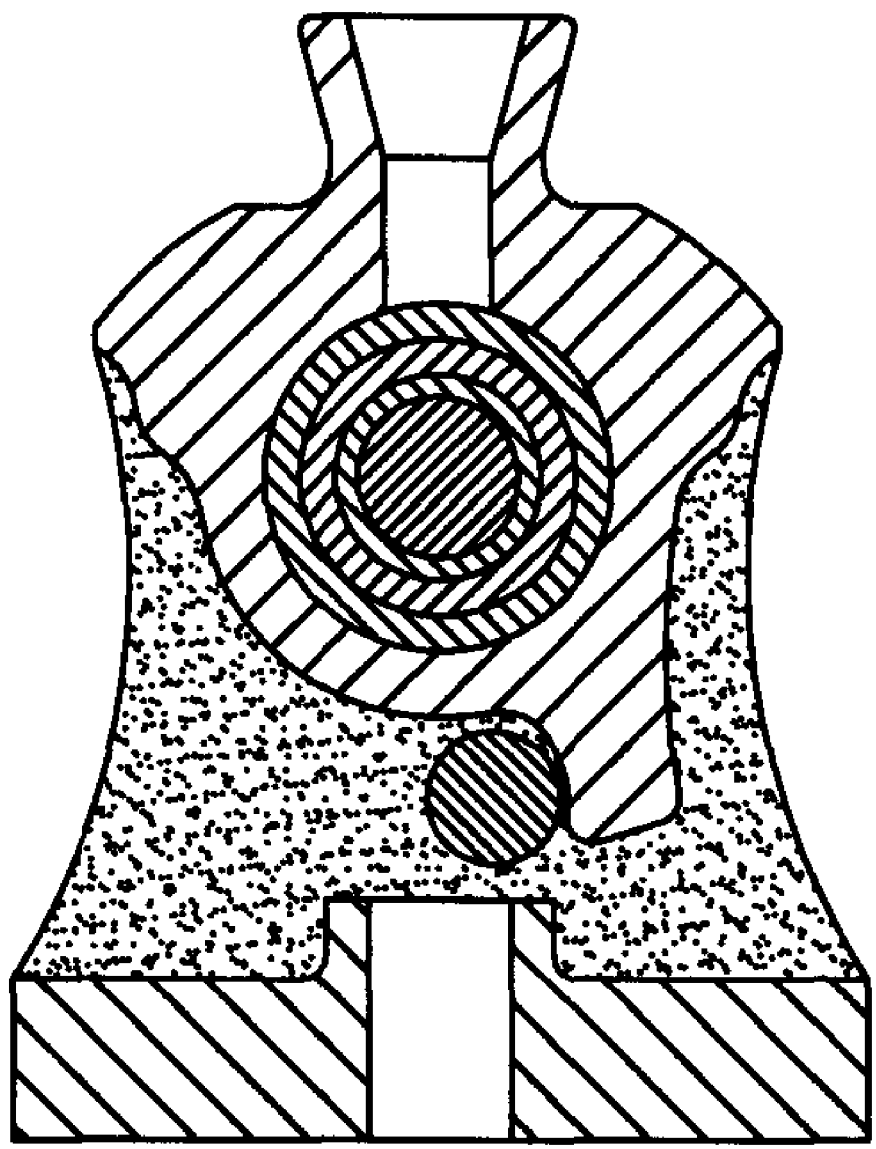
FIG. 30 is a sectional side elevation view of the multi-axis prosthetic ankle of FIG. 21, taken along lines D-D thereof.
Figure 34:
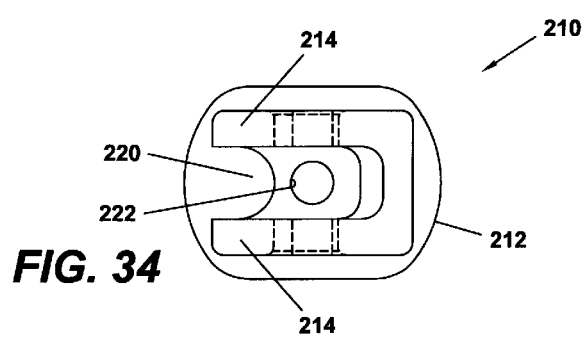
FIG. 34 is a top plan view of a prosthetic foot connection component of the multi-axis prosthetic ankle of FIG. 31.
Figure 35:
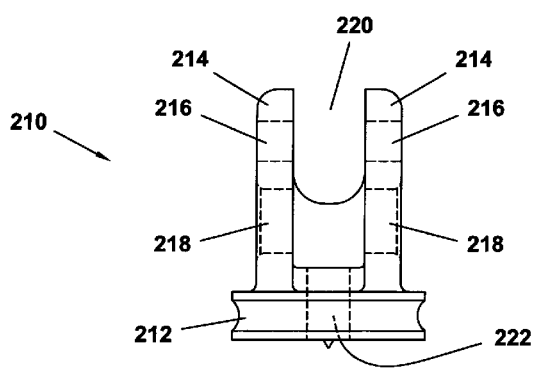
FIG. 35 is a front elevation view of the prosthetic foot connection component of FIG. 34.
Figure 36:
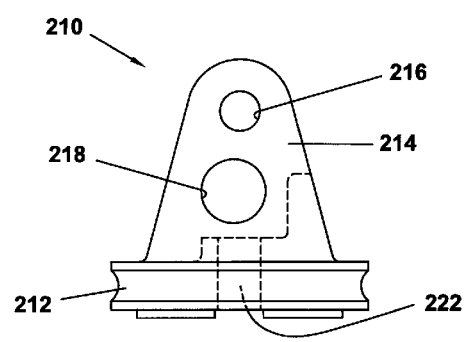
FIG. 36 is a side elevation view of the prosthetic foot connection component of FIG. 34.
Figure 37:
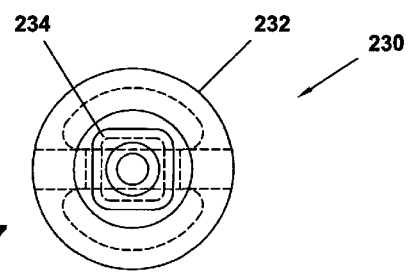
FIG. 37 is a top plan view of a lower leg connection component of the multi-axis prosthetic ankle of FIG. 31.
Figure 38:
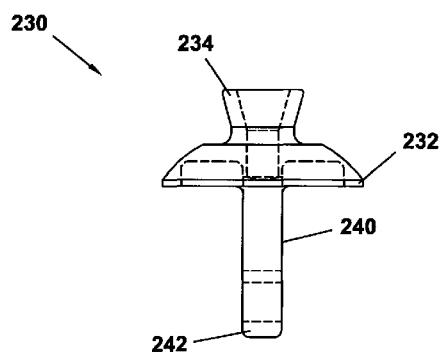
FIG. 38 is a front elevation view of the lower leg connection component of FIG. 37.
Figure 39:
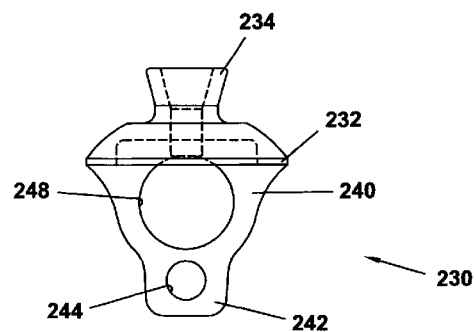
FIG. 39 is a side elevation view of the lower leg connection component of FIG. 37.
Figure 40:
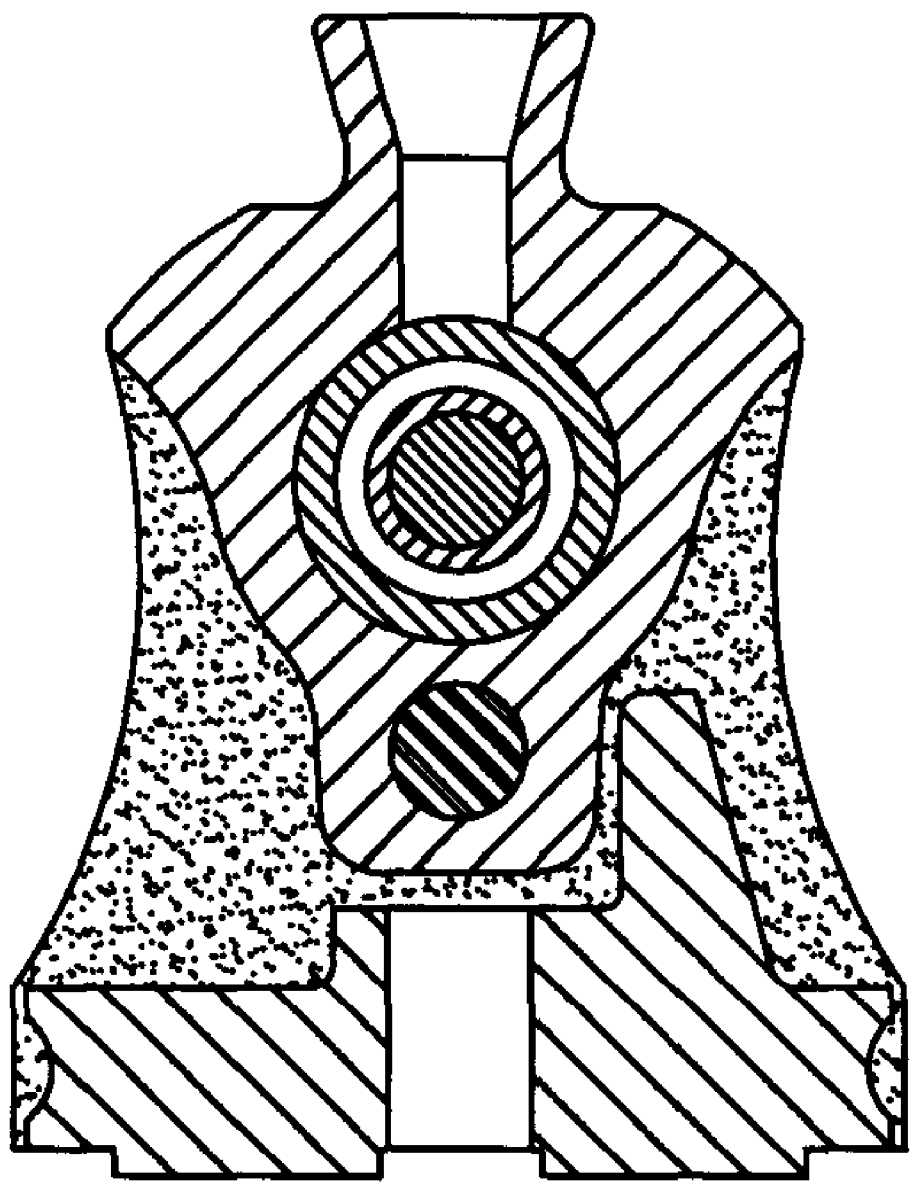
FIG. 40 is a sectional side elevation view of the multi-axis prosthetic ankle of FIG. 31, taken along lines E-E thereof.

The ankle 100 is assembled by installing the lower leg connection component 130 to the prosthetic foot connection component 110. While it is described that the lower leg connection component 130 is "installed" to the prosthetic foot connection component 110, it should be realized that there is no direct connection of the components. Rather, "installed" merely refers to positioning the lower leg connection component 130 such that the connecting projection 140 properly resides within the receiving cavity 114. This relationship can best be observed by reference to the sectional view of FIG. 30. As can be seen, when the components 110, 130 are properly arranged, the ledge 144 on the protrusion 142 of the connecting projection 140 is preferably in close proximity to a stop 126 formed by a recess 122 in a posterior vertical wall 112 of the body component, thereby permitting only a small amount of elastomeric material will be present between the ledge and the stop. Simultaneously, the base 132 of the lower leg connection component 130 is substantially parallel to the top surface 120 of the prosthetic foot connection component 110. Hence, it can be understood that the prosthetic foot connection component 110 and the lower leg connection component 130 are not in direct contact. In an alternate embodiment, the prosthetic foot connection component 110 and the lower leg connection component 130 may be arranged such that the finalized ankle 100 has a larger amount of elastomeric material residing between the ledge 144 and the stop 126.

Accordingly, by the above-described arrangements of the prosthetic foot connection component 110 and the lower leg connection component 130, there will generally be a gap between a bottom surface 134 of the lower leg connection component base 132 and the top surface 120 of the prosthetic foot connection component 110. A flexion stop 136 is preferably located within this gap. The flexion stop 136 may be a separate component, or may be integrated or otherwise affixed to the prosthetic foot connection component 110. The flexion stop 136 may be of circular cross section to receive a portion of the disk-like base 132 of the lower leg connection component 130. The flexion stop 136 operates as a limit to flexion of the ankle.

Subsequent to installation of the lower leg connection component 130 and the flexion stop 136 to the prosthetic foot connection component 110, the assembly thereof is placed within a mold (not shown). The mold is adapted to maintain the lower leg connection component 130 and the prosthetic foot connection component 110 substantially in the position shown in FIG. 30, and described above. With the components 110, 130 held in this position, an elastomeric material, preferably in a flowable state, is injected or otherwise introduced into the mold and permitted to solidify. The elastomeric material is preferably a rubber, and more preferably a thermoset rubber polymer having a high resistance and memory under cyclical loading. Non-limiting examples include butyl rubber, ethylene-propylene rubber, neoprene rubber, nitrile rubber, polybutadiene rubber, polyisoprene rubber, stereo rubber, styrene-butadiene rubber, natural rubber, or a combination of two or more of these rubbers.

The elastomeric material thereby encases and/or bonds to the prosthetic foot connection component 110 and the lower leg connection component 130. The elastomeric material may also encase and/or bond to the flexion stop 136. Introducing the elastomeric material to the component assembly in this manner allows the elastomeric material to form a casing 146 around the components (or portions thereof), and to fill voids between the components. For example, any space within the cavity 114 that is not occupied by the connecting projection 140 will be filled with the elastomeric material. Consequently, a flexible ankle assembly is produced through retention of the ankle components by the elastomeric material. The flexibility of the assembly allows for a smooth transition through the entire gait cycle of a user of the ankle, from heel strike, through midstance, to toe off. As can be better understood by reference to FIG. 30, the prosthetic foot connection component 110 and the lower leg connection component 130 are not directly connected to one another but, instead, are floatingly connected through the intermediary elastomeric material casing 146. For purposes of adhesion, the peripheral surface of at least the prosthetic foot connection component 110 may have one or more recesses 110a. These recesses improve the grip of the elastomeric material bonded to the exterior of the prosthetic foot connection component 110.

Once the above-described assembly and molding process is accomplished, the completed multi-axis ankle assembly 100 can be attached between a prosthetic socket and prosthetic foot.

The angular degree of rotational motion between the prosthetic foot connection component 110 and the lower leg connection component 130 is preferably limited by fixed (mechanical) stops. In one embodiment, the fixed stops are formed by a combination of the abutment of the elastomeric material covered ledge 144 with the elastomeric material covered stop 126, and contact between the base 132 of the lower leg connection component with the flexion stop 136 or the top surface 120 of the prosthetic foot connection component 110. The fixed stop provided by abutment of the ledge 144 with the recess 122 in the wall 112 of the prosthetic foot connection component 110 is used to control the amount of toe lift that a prosthetic foot attached to the ankle 100 may experience.

During ambulation, compression of the elastomeric material resists movement (pivoting) of the ankle 100. The compression resistance of the elastomeric material increases as the angle of ankle 100 pivot increases. When this resistance is equivalent to the turning (pivoting) load on the ankle 100, the elastomeric material may also act as a fixed stop against further rotation. One skilled in the art can use data regarding the expected load on the ankle 100 and the compression resistance of the elastomeric material to optimize the design of the ankle.

Figure 20:
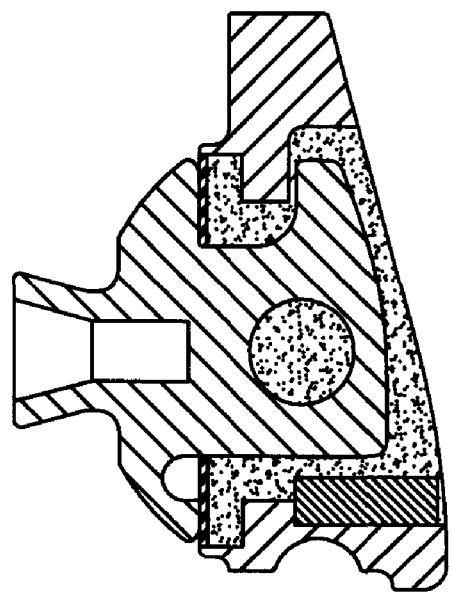
FIG. 20 depicts an alternate embodiment of the sectional side elevation view of FIG. 19, wherein a reinforcing section and a retaining pin has been added to the prosthetic foot connection component.
Figure 19:
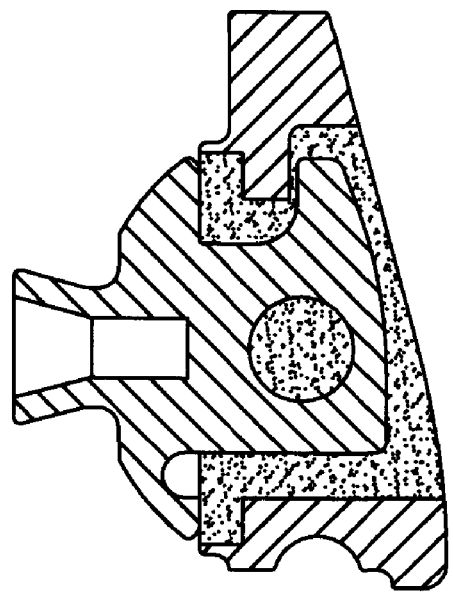
FIG. 19 is a sectional side elevation view of the multi-axis prosthetic ankle of FIG. 10, taken along lines C-C thereof.
Figure 24:
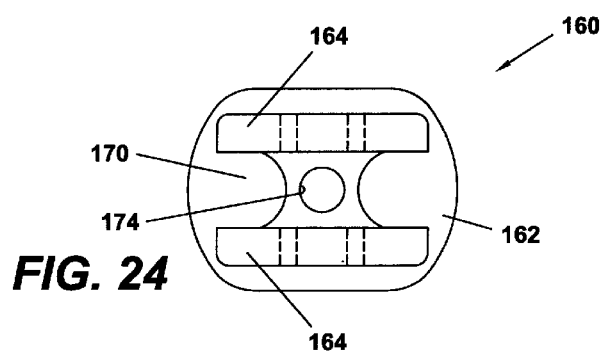
FIG. 24 is a top plan view of a prosthetic foot connection component of the multi-axis prosthetic ankle of FIG. 21.
Figure 25:
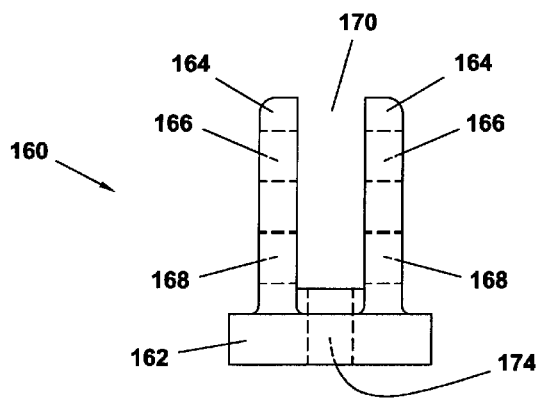
FIG. 25 is a front elevation view of the prosthetic foot connection component of FIG. 24.
Figure 26:
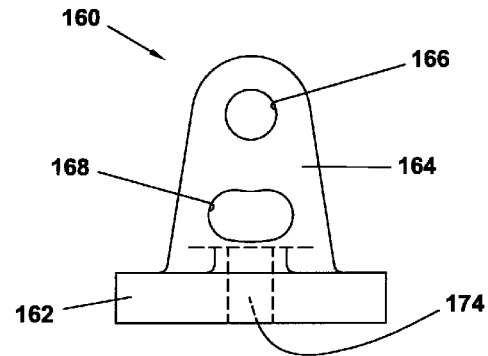
FIG. 26 is a side elevation view of the prosthetic foot connection component of FIG. 24.

As can be seen in the sectional view of FIG. 20, a reinforcing material 124 can be installed to the top surface 120 of the prosthetic foot connection component 110. Alternatively, the reinforcing material 124 may be installed to the top surface of the dorsi-flexion stop 136. The reinforcing material 124 acts to protect the elastomeric material from erosion due to contact with the moving base 132 of the lower leg connection component 130. The reinforcing material 124 may be, for example, a section of Kevlar® mat, or a may be comprised of another similarly abrasion resistant material, or combination of materials.

As can also be seen in the sectional view of FIG. 20, a locking pin 128 or similar element may be optionally inserted into the prosthetic foot connection component 110 after the connecting projection 140 of the lower leg connection component 130 is inserted into the cavity 114 therein. The locking pin 128 ensures that the connecting projection 140 cannot be withdrawn from the cavity 114. Consequently, the locking pin 128 also ensures that the prosthetic foot connection component 110 and the lower leg connection component 130 cannot thereafter be separated.

The ankle 100 according to this embodiment of the present invention has a higher load range of increasing moment of resistance compared to prior art ankles, which flatten out over lower load ranges. Exemplary limits of movement permitted by the stops of this particular ankle 100 are as follows:

Internal/External rotation: 18°/18° (360 total).
Plantar flexion: 15°.
Dorsi flexion: 5°.
Inversion/Eversion: 5°/5° (100 total).
Anterior/Posterior translation: 0.0 to 0.05 inches.
Medial/Lateral translation: 0.00 to 0.05 inches.
Vertical displacement: 0.07 inches.

It should be understood that the above limits of movement have been provided for purposes of illustration only, and the ankle 100 to which the limits apply can be designed to have other limits of movement as well.

As can be understood from a reading of the above description and reference to the drawing figures related to the ankles 5, 100, during walking, relative motion (translation and multi-axis rotation) between the component 10, 110 mounted to the prosthetic foot, and the component 20, 130 coupled to the prosthetic socket is permitted by the elastic deformation of the elastomeric material. The motion is thus polycentric and multi-axial, with no fixed center of rotation or translation. Moreover, surface-to-surface contact that could lead to a breakdown of the material used to manufacture the rigid components of each ankle 5, 100 has been eliminated. For example, even the small gap between the ledge 144 and the stop 126 is preferably filled with elastomeric material. In addition to allowing relative motion (translation and multi-axis rotation) between the component 10, 110 mounted to the prosthetic foot and the component 20, 130 coupled to the prosthetic socket, the elastomeric material also absorbs impact energies and, therefore, further acts as a vibration dampening device.

Variations of yet another embodiment of a multi-axis prosthetic ankle 150, 200 of the present invention are illustrated in FIGS. 21-30 and 31-41, respectively. Unlike the previously-described prosthetic ankles 5, 100, these embodiments of the multi-axis prosthetic ankle 150, 200 employ a direct mechanical connection between components thereof.

The multi-axis prosthetic ankle 150 of FIGS. 21-30 can be seen to include a bottom, prosthetic foot connection component 160, that is adapted for attachment to a prosthetic foot, and a lower leg connection component 180 that is adapted to couple the ankle 150 to a prosthetic socket component, such as by means of a prosthetic pylon or the like.

The prosthetic foot connection component 160 is essentially formed by a pair of spaced apart and upwardly-extending support arms 164, having a first end thereof attached to a base 162. The base 162 and the pair of support arms 164 combine to form a mounting bracket for attaching the ankle 150 to a prosthetic foot, and for pivotally retaining the lower leg connection component 180. A retaining pin receiving aperture 166 is located in each of the upwardly-extending support arms 164. As can be best observed in FIGS. 23 and 26, a dorsi-flexion limiting slot 168 is also located in each of the upwardly-extending support arms 164. A threaded or unthreaded bore(s) 174 may be located in the base 162 to facilitate attachment of the ankle 150 to a prosthetic foot. The prosthetic foot connection component 160 may be integrally formed of aluminum, but can also be formed or machined from other rigid materials, including titanium, stainless steel, or rigid plastic, for example.

A space 170 between the pair of support arms 164 is provided to receive a downwardly-extending connecting projection 190 of the lower leg connection component 180. More specifically, the space 170 between the pair of support arms 164 is designed to allow the connecting projection 190 of the lower leg connection component 180 to reside therein, while maintaining some predetermined space between each support arm. As will be explained in more detail below, the connecting projection 190 is mechanically coupled to the support arms 164 of the prosthetic foot connection component 160 in this embodiment of the ankle 150. During ambulation of the user, the connecting projection 190 is able to move within the space 170, allowing for flexion of the ankle 150.

Figure 27:
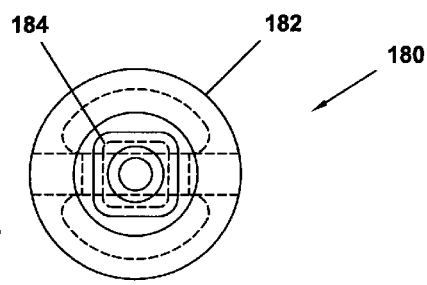
FIG. 27 is a top plan view of a lower leg connection component of the multi-axis prosthetic ankle of FIG. 21.
Figure 28:
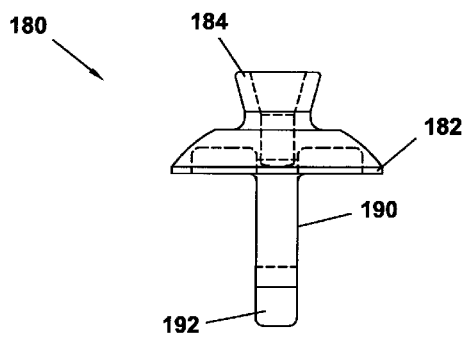
FIG. 28 is a front elevation view of the lower leg connection component of FIG. 27.
Figure 29:
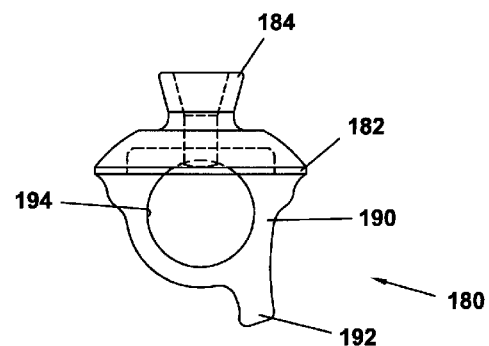
FIG. 29 is a side elevation view of the lower leg connection component of FIG. 27.

As can best be observed in FIGS. 27-29, this embodiment of the lower leg connection component 180 may have a generally circular, disk-like base 182—although other shapes are also possible. A pyramid part 184 may project upward from a central dome-like portion of the base. The pyramid part 184 may be of a generally conventional design.

Extending downward from the base 182 of the lower leg connection component 180 is the connecting projection 190. The connecting projection 190 is provided to pivotally connect the lower leg connection component 180 to the prosthetic foot connection component 160. The connecting projection 190 is a rigid component, and is firmly affixed to the base 182. Preferably, the connecting projection 190 is integrally formed with the base 182, such as by molding or machining. In this particular embodiment, the connecting projection 190 is shown to have a body that is generally rectangular in shape, except for a protrusion 192 extending from a lower portion thereof. The connecting projection 190 is also shown to have a thickness that is less than the space 170 between the support arms 164. It should be understood, however, that the connecting projection 190 can be of virtually any size and shape that allows it to adequately move within the space 170 between the support arms 164. An aperture, preferably a bearing receiving aperture 194, is located in the connecting projection 190 such that its center will align with the aligned centerlines of the retaining pin receiving apertures 166 in the prosthetic foot connection component support arms 164.

In this embodiment of the ankle 150, the protrusion 192 extends sufficiently from the main body of the connecting projection 190 such that, after ankle assembly, the protrusion will pass over at least a portion of the dorsi-flexion limiting slots 168 when the ankle is pivoted about its retaining pin. The dorsi-flexion limiting slots 168 are adapted to moveably retain a dorsi-flexion limiting pin 172. The dorsi-flexion limiting slots 168 and dorsi-flexion limiting pin 172 operate in conjunction with an elastomeric material to help control and limit dorsi-flexion of the ankle (as described in more detail below).

The lower leg connection component 180 is also preferably integrally formed of titanium, but can be formed or machined from other rigid materials, including, stainless steel, aluminum, or rigid plastic, for example.

The ankle 150 is assembled by first installing a bearing 196 to the bearing receiving aperture 194 (when a bearing is used) of the connecting projection 190. Preferably, the bearing 196 is a spherical bearing to allow for a greater range of motion of the lower leg connection component 180. Preferably, the bearing 196 is force or press fit into the bearing receiving aperture 194 of the projecting connection 190. With the bearing 194 in place, the projecting connection 190 is inserted into the space 170 between the support arms 164 of the prosthetic foot connection component 160, such that the retaining pin receiving apertures 166 in the support arms are aligned with the bore in the bearing. With the components thus aligned, a retaining pin 198 is inserted through the receiving apertures 166 and the bearing 196. Preferably, the receiving apertures 166 are sized so as to securely grip the ends of the retaining pin 198 once it is installed. Alternatively, clips or other retainers could be installed on the ends of the pin 198 to maintain the position thereof. As can be best observed by reference to FIG. 22, when properly installed, the connecting projection 190 and the bearing 196 should be substantially centered along the length of the retaining pin 198 and within the space 170 between the support arms 164 of the prosthetic foot connection component 160.

The dorsi-flexion limiting pin 172 may next be installed into the dorsi-flexion limiting slot 168, although such may be accomplished prior to assembly of the components 160, 180, as well. In a neutral position of the assembled ankle 150, the protrusion 192 is in contact with the dorsi-flexion limiting pin 172 while the dorsi-flexion limiting pin resides at a posterior end of the dorsi-flexion limiting slot 168, and while the base 182 of the lower leg connection component 180 is substantially level. The neutral position of the assembled ankle 150 can best be observed by reference to FIGS. 23 and 30. It is generally preferred that a small amount of elastomeric material exist between the protrusion 192 and the dorsi-flexion limiting pin 172, and between the flexion limiting pin and the walls of the flexion limiting slots 168.

Subsequent to coupling of the prosthetic foot connection component 160 to the lower leg connection component 180, and installation of the dorsi-flexion limiting pin 198, the assembly of components is placed within a mold (not shown). The mold is adapted to maintain the components in the neutral position shown in FIGS. 23 and 30, and described above. With the components held in this position, an elastomeric material in a flowable state is injected or otherwise introduced into the mold and permitted to harden. The elastomeric material is preferably a rubber, and more preferably a thermoset rubber polymer having a high resistance and memory under cyclical loading. Non-limiting examples include butyl rubber, ethylene-propylene rubber, neoprene rubber, nitrile rubber, polybutadiene rubber, polyisoprene rubber, stereo rubber, styrene-butadiene rubber, natural rubber, or a combination of two or more of these rubbers.

The elastomeric material thereby forms a casing 188 around, and/or bonds to the prosthetic foot connection component 160 and the lower leg connection component 180. The elastomeric material also encases and bonds to the dorsi-flexion limiting pin 172, the spherical bearing 196 (if present), and the retaining pin 198, and fills in the space 170 between the support arms 164 and the unoccupied portion of the dorsi-flexion limiting slots 168.

Once the above-described assembly and molding process is accomplished, the completed multi-axis ankle assembly 150 can be installed between a prosthetic socket and prosthetic foot in a conventional manner.

Introducing the elastomeric material to the component assembly in the above-described manner allows the elastomeric material to provide a controlling resistance to plantar flexion, dorsi flexion, inversion, eversion, translation and internal/external rotational movement of a prosthetic foot to which the ankle 150 is attached. Resistance to such movement is provided by a corresponding compression of the elastomeric material. The compression resistance of the elastomeric material increases as the angle of ankle 150 pivot increases. When this resistance is equivalent to the turning (pivoting) load on the ankle 150, the elastomeric material may act as a fixed stop against further rotation. One skilled in the art can use data regarding the expected load on the ankle 150 and the compression resistance of the elastomeric material to optimize the design of the ankle. Dorsi-flexion is further controlled through resistance to movement of the protrusion 192 by the elastomerically held dorsi-flexion limiting pin 172. The dorsi-flexion limiting pin 172 also acts as a fixed stop to dorsi-flexion when the elastomeric material residing in the flexion limiting slots 168 reaches its compression limit. Hard (mechanical) stops to movement of the ankle 150 may also be provided by the elastomeric material covered inward-facing walls of the support arms 164, and/or by spanning the space between the support arms with a web of rigid material.

It should be further understood that the total amount of dorsi-flexion can be controlled by adjusting the length of the dorsi-flexion limiting slot 168. For example, shortening the dorsi-flexion limiting slot 168 will result in a reduction in the total amount of dorsi-flexion that can be provided by the ankle 150. Conversely, lengthening the dorsi-flexion limiting slot 168 will result in an increase in the total amount of dorsiflexion that can be provided by the ankle 150.

The design of the ankle 150, in conjunction with use of the elastomeric material, allows for a smooth transition through the entire gait cycle of a user of the ankle; from heel strike, through midstance, to toe off. In addition, the elastomeric material absorbs impact energies and, therefore, also acts as a vibration dampening device.

As can be understood from the foregoing description, the prosthetic foot connection component 160 and lower leg connection component 180 of the ankle 150 are mechanically connected to one another via the retaining pin 198. When no spherical bearing is used, movement such as internal/external rotation, inversion/eversion, and medial/lateral translation may be permitted by providing an aperture in the connecting projection 180 that is sized to allow relative movement of the connecting projection about the retaining pin 198. When used, the spherical bearing 196 facilitates such ankle movement, and in a more controlled manner. Use of the spherical bearing 196 and the elastomeric material, and provision of the space 170 between the connecting projection 190 and the support arms 164 additionally minimizes or eliminates surface-to-surface contact between the components. Therefore, the design of the ankle 150 also reduces or eliminates the type of surface-to-surface contact that could lead to a breakdown of the material used to manufacture the rigid components of the ankle.

The ankle 150 according to this embodiment of the present invention has a higher load range of increasing moment of resistance compared to prior art ankles, which flatten out over lower load ranges. Exemplary limits of movement permitted by the stops of this particular embodiment of the ankle 150 are as follows:

Internal/External rotation: 5°/5° (100 total).
Plantar flexion: 13°.
Dorsi flexion: 4°.
Inversion/Eversion: 8°.
Anterior/Posterior translation: None.
Medial/Lateral translation: 0.00 to 0.05 inches.
Vertical displacement: None.

It should be understood that the above limits of movement have been provided for purposes of illustration only, and the ankle 150 to which the limits apply can be designed to have other limits of movement as well.

Like the multi-axis prosthetic ankle 150 of FIGS. 21-30, the multi-axis prosthetic ankle 200 of FIGS. 31-41 can be seen to include a bottom, prosthetic foot connection component 210 that is adapted for attachment to a prosthetic foot, and a lower leg connection component 230 that is adapted to couple the ankle 200 to a prosthetic socket component, such as by means of a prosthetic pylon or the like.

The prosthetic foot connection component 210 is essentially formed in a like manner to the prosthetic foot connection component 160 of the ankle 150 of FIGS. 21-30: with a pair of spaced apart and upwardly-extending support arms 214, having one end thereof attached to a base 212. The base 212 and the pair of support arms 214 again combine to form a mounting bracket for attaching the ankle 200 to a prosthetic foot, and for pivotally retaining the lower leg connection component 230. A space 220 is formed between the support arms 214 for receiving a connecting projection 240 of the lower leg connection component 230. A retaining pin receiving aperture 216 is located in each of the upwardly-extending support arms 214. As can be best observed in FIGS. 33 and 36, a flexion limiting aperture 218 is also located in each of the upwardly-extending support arms 214. A threaded or unthreaded bore(s) 222 may be located in the base 212 to facilitate attachment of the ankle to a prosthetic foot.

This embodiment of the lower leg connection component 230 may also have a generally circular, disk-like base 232, although other shapes are also possible. The base 232 may have a pyramid part 234 projecting upward from a dome-like central portion thereof. The pyramid part 234 can be used to connect the ankle 200 to a prosthetic pylon or some other component that acts to couple the ankle to the prosthetic socket. The pyramid part 234 may be of a generally conventional design.

Extending downward from the base 232 of the lower leg connection component 230 is a connecting projection 240, that is again provided to pivotally connect the lower leg connection component 230 to the prosthetic foot connection component 210. The connecting projection 240 is again rigid component that is firmly affixed to, or integrally formed with the base 232. In this particular embodiment, the connecting projection 240 is shown to have a body that tapers inward as it extends downward from its point of connection to the base 232, toward its distal end 242. An aperture, preferably a bearing receiving aperture 248 is located in the connecting projection 240 such that its center will align with the aligned centerlines of the retaining pin receiving apertures 216 in the prosthetic foot connection component support arms 214. A pin receiving aperture 244 is located near the distal end 242 of the connecting projection to receive a flexion limiting pin 246. The connecting projection 240 is again shown to have a thickness that is less than the space 220 between the support arms 214. It should be understood, however, that the connecting projection 240 can be of virtually any size and shape that allows it to adequately move within the space 220 between the support arms 214.

The prosthetic foot connection component 210 is preferably formed of aluminum, while the lower leg connection component 230 is preferably formed of titanium. However, each component 210, 230 can also be formed or machined from other rigid materials, including titanium, stainless steel, aluminum, or rigid plastic, for example.

The ankle 200 shown in FIGS. 31-41 is assembled in substantially the same manner as the ankle 150 shown in FIGS. 21-30. The primary difference between the two ankles is that a flexion limiting pin 246 is installed to the connecting projection 240 of this embodiment of the ankle 200, as opposed to installation of a flexion limiting pin 172 to the slot 168 in the support arms 164 of the previously described ankle 150. Hence, once the prosthetic foot connection component 210 and the lower leg connection component 230 of the ankle 200 have been connected using the retaining pin 198, the flexion limiting pin 246 is passed through the flexion limiting aperture 218 in one of the support arms 214 and installed to the pin receiving aperture 244 in the connecting projection 240. Preferably, the flexion limiting pin 246 is retained by the connecting projection 240 in a position such that each end of the pin resides at least partially within a corresponding one of the flexion limiting apertures 218. Preferably, the flexion limiting pin 246 is force or press fit to the pin receiving aperture 244 so that it cannot be easily dislodged.

In a neutral (midstance) position of this embodiment of the assembled ankle 200, the base 232 of the lower leg connection component 230 is substantially level, and the ends of the flexion limiting pin 246 reside within the flexion limiting apertures 218 in corresponding support arms 214. The neutral position of the assembled ankle 200 can best be observed by reference to FIGS. 33, 40 and 41a.

Subsequent to coupling of the prosthetic foot connection component 210 to the lower leg connection component 230, and installation of the flexion limiting pin 246, the assembly of components is placed within a mold (not shown). The mold is preferably adapted to maintain the components in the neutral position shown in FIGS. 33, 40 and 41*a*, and described above. With the components held in this position, an elastomeric material in a flowable state is injected or otherwise introduced into the mold and permitted to harden. The elastomeric material is preferably a rubber, and more preferably a thermoset rubber polymer having a high resistance and memory under cyclical loading. Non-limiting examples include butyl rubber, ethylene-propylene rubber, neoprene rubber, nitrile rubber, polybutadiene rubber, polyisoprene rubber, stereo rubber, styrene-butadiene rubber, natural rubber, or a combination of two or more of these rubbers. It is also possible to mold the components while they are maintained in a flexed state. More specifically, the components may be molded in a position such that the resulting ankle will have a raised heel when in its neutral position. Such an ankle may be particularly appropriate for use with boots, high heel shoes, and other footwear having a similar forward slope.

The elastomeric material thereby forms a casing 250 around, and/or bonds to, the prosthetic foot connection component 210 and the lower leg connection component 230. The elastomeric material also encases and bonds to the flexion limiting pin 246, the spherical bearing 196 (if used) and the retaining pin 198, and fills in the space 220 between the support arms 214 and the unoccupied portion of the flexion limiting apertures 218.

Once the above-described assembly and molding process is accomplished, the completed multi-axis ankle assembly 200 can be installed between a prosthetic socket and prosthetic foot in a conventional manner.

Introducing the elastomeric material to the component assembly in this manner allows the elastomeric material to provide a controlling resistance to plantar flexion, dorsi flexion, inversion, eversion, translation and internal/external rotational movement of a prosthetic foot to which the ankle 200 is attached. Resistance to such movement is provided by a corresponding compression of the elastomeric material. The compression resistance of the elastomeric material increases as the angle of ankle 200 pivot increases. When this resistance is equivalent to the turning (pivoting) load on the ankle 200, the elastomeric material may act as a fixed stop against further rotation. One skilled in the art can use data regarding the expected load on the ankle 200 and the compression resistance of the elastomeric material to optimize the design of the ankle.

Figure 41C:
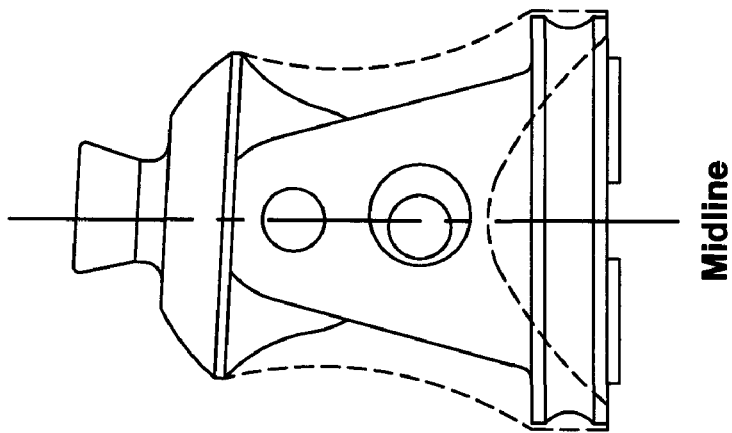
FIG. 41*c* shows the multi-axis prosthetic ankle of FIG. 32 in a toe-off position.
Figure 41A:
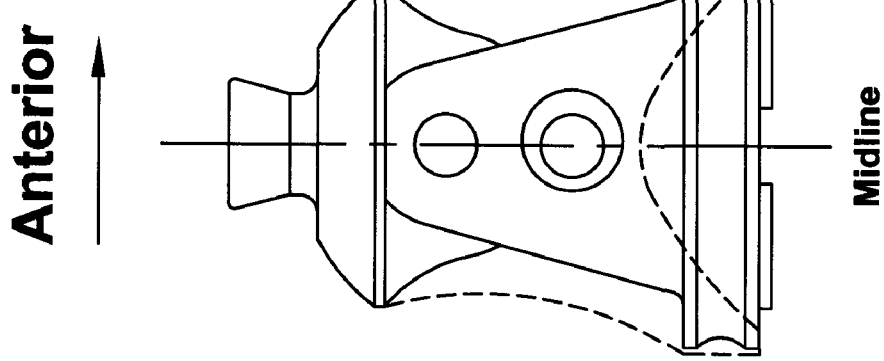
FIG. 41*a* shows the multi-axis prosthetic ankle of FIG. 32 in a mid-stance position.
Figure 41B:
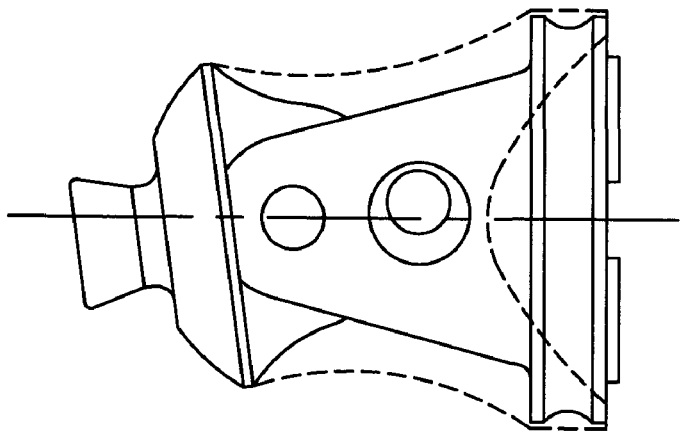
FIG. 41*b* shows the multi-axis prosthetic ankle of FIG. 32 in a heel strike position.
Figure 42:
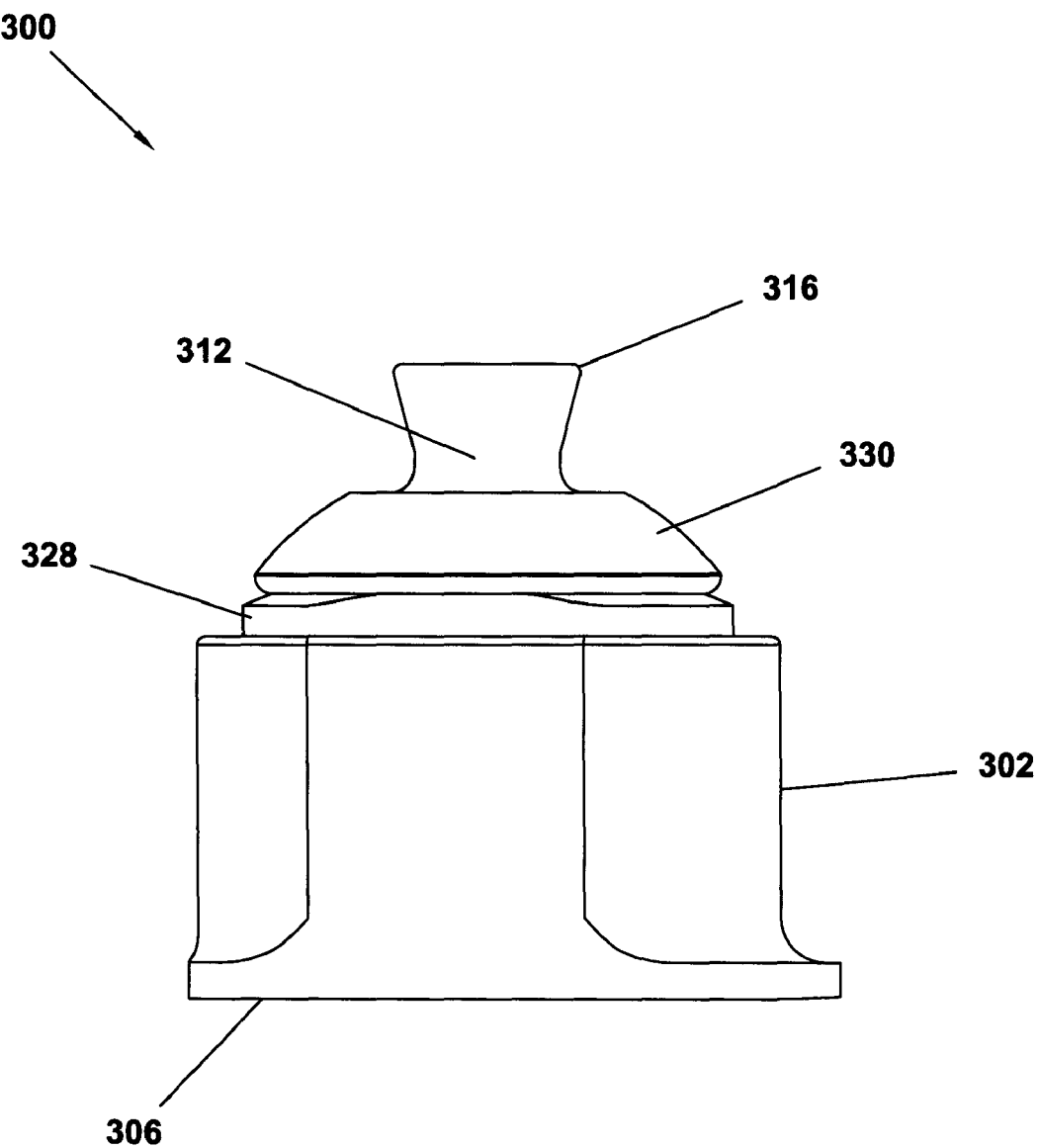
FIG. 42 is a side elevational view of still another exemplary embodiment of a multi-axis prosthetic ankle of the present invention.

In this embodiment of the ankle 200, the limit of both dorsi-flexion and plantar-flexion is further controlled by the size and location of the flexion limiting aperture 218 in the support arms 214. As can be best understood by reference to FIGS. 33, 40, and 41*a*-41*c*, a flexion limiting aperture 218 of smaller diameter would allow for less total dorsi/plantar-flexion, while a flexion limiting aperture 218 of greater diameter would allow for more total dorsi/plantar flexion. Additionally, each of dorsi-flexion and plantar-flexion can be allocated a different percentage of the total available movement in such direction. For example, when the center of each flexion limiting aperture 218 is located at the mid-line of the support arms 214 (i.e., substantially in line with the center of the retaining pin 198), the amount of dorsi-flexion and plantar-flexion will be essentially equal. By shifting the center of the flexion limiting apertures 218 toward the anterior or posterior of the ankle 200, however, the amount of dorsi-flexion and plantar-flexion can be made to be unequal. For example, as shown in FIGS. 41*a*-41*c*, the flexion limiting apertures 218 are shifted slightly anterior to the midline of the ankle 200, which results in a total amount of possible plantar-flexion that is greater than the total possible amount of dorsi-flexion. As shown in FIGS. 41*a*-41*c*, the diameter and location of the flexion limiting apertures 218 of this particular embodiment of the ankle 200 provides for approximately 12 degrees of maximum flexion at heel strike and approximately 3 degrees of maximum flexion at toe off, for a total of 15 degrees of total movement in the dorsi/plantar-flexion plane. Therefore, as can be understood, greater or lesser amounts of dorsi-flexion and/or plantar-flexion are possible by altering the diameter and/or location of the flexion limiting apertures 218. It should also be understood that a similar adjustment to dorsi-flexion and/or plantar-flexion can be achieved by manipulating the size and/or location of the flexion limiting pin 246, instead of the flexion limiting apertures 218. Alternatively, an adjustment to the size and/or location of both the flexion limiting apertures 218 and the flexion limiting pin 246 can also be made for this purpose.

It should also be realized that resistance to dorsi-flexion and plantar-flexion occurs both as a result of compression of the elastomeric material by the connecting projection 240, and by compression of the elastomeric material by the flexion limiting pin 246. Thus, the flexion limiting pin 246 not only acts as a fixed stop when it causes the elastomeric material in the flexion limiting apertures 218 to reach its compression limit, it also acts as a means of controlled resistance to dorsi/plantar-flexion.

The design of the ankle 200, in conjunction with use of the elastomeric material, allows for a smooth transition through the entire gait cycle of a user of the ankle; from heel strike, through midstance, to toe off. In addition, the elastomeric material absorbs impact energies and, therefore, also acts as a vibration dampening device.

As can be understood from the foregoing description, the prosthetic foot connection component 210 and lower leg connection component 230 of the ankle 200 are mechanically connected to one another via the retaining pin 198. When no spherical bearing is used, movement such as internal/external rotation, inversion/eversion, and medial/lateral translation may be permitted by providing an aperture in the connecting projection 240 that is sized to allow relative movement of the connecting projection about the retaining pin 198. When used, the spherical bearing 196 facilitates such ankle movement, and in a more controlled manner. Use of the spherical bearing 196 and provision for the space 220 between the connecting projection 240 and the support arms 214 additionally minimizes surface-to-surface contact between the components. Additionally, the flexion limiting pin's 246 compression of the elastomeric material within the flexion limiting apertures 218 can act as a hard stop, instead of compression of the elastomeric material in the space 220 by the connecting projection 240. Therefore, the design of the ankle 200 also reduces or eliminates the type of surface-to-surface contact that could lead to a breakdown of the material used to manufacture the rigid components of the ankle.

The ankle 200 according to this embodiment of the present invention has a higher load range of increasing moment of resistance compared to prior art ankles, which flatten out over lower load ranges. Exemplary limits of movement permitted by the stops of this particular embodiment of the ankle 200 are as follows:

Internal/External rotation: 5°/5° (100 total).
Plantar flexion: 13°.
Dorsi flexion: 4°.
Inversion/Eversion: 8°.
Anterior/Posterior translation: None.
Medial/Lateral translation: 0.0 to 0.05 inches.

Vertical displacement: None.

It should be understood that the above limits of movement have been provided for purposes of illustration only, and the ankle 200 to which the limits apply can be designed to have other limits of movement as well.

Still another embodiment of a multi-axis prosthetic ankle 300 of the present invention is illustrated in FIGS. 42-46. This embodiment of a multi-axis prosthetic ankle 300 can be seen to again include a bottom, prosthetic foot connection component 302, that is adapted for attachment to a prosthetic foot, and a lower leg connection component 312 that is adapted for coupling of the ankle to a prosthetic socket, such as by means of a pylon or other suitable component.

The prosthetic foot connection component 302 of this embodiment is essentially a substantially hollow housing having rigid side walls 304 that bound a receiving cavity 308. The prosthetic foot connection component 302 may also have a partial or complete bottom wall. As shown, the prosthetic foot connection component 302 has a bottom wall 306 with an aperture 310 passing therethrough. Threaded or unthreaded bores 334 may also be provided in or through the prosthetic foot connection component 302 to facilitate its attachment to a prosthetic foot. In an embodiment of a prosthetic foot connection component having a complete, or substantially complete bottom wall, a single threaded or unthreaded bore may be present approximately at its center point. The prosthetic foot connection component 302 may be integrally formed of various materials such as, for example, titanium, stainless steel, aluminum, rigid plastic or other suitable rigid materials.

The receiving cavity 308 of the prosthetic foot connection component 302 is designed to receive a portion of a lower leg connection component 312. The receiving cavity 308 may also be designed to receive one or more retaining elements, examples of which are described in more detail below. During ambulation of a user, the lower leg connection component 312 is able to move within the receiving cavity 308 in a manner that allows for flexion of the ankle 300.

The lower leg connection component 312 is generally comprised of an elongated element having a first, or distal end 312a adapted to reside in the receiving cavity 308 after ankle assembly, and a second, or proximal end 312b adapted to reside outside the receiving cavity 308 after ankle assembly. The distal end 312a of the lower leg connection component 312 is preferably designed to facilitate retention of the lower leg connection component in the receiving cavity. The proximal end 312b of the lower leg connection component 312 is preferably adapted for attachment to a prosthetic pylon or some other component used to couple the ankle to a prosthetic socket. In the particular embodiment of the present invention, the proximal end 312b of the lower leg connection component 312 is comprised of a pyramid adapter 316. It should be realized, however, that other types of connecting devices may also be used. The lower leg connection component 312 may be formed from materials alike or similar to the materials used to form the prosthetic foot connection component.

Figure 43:
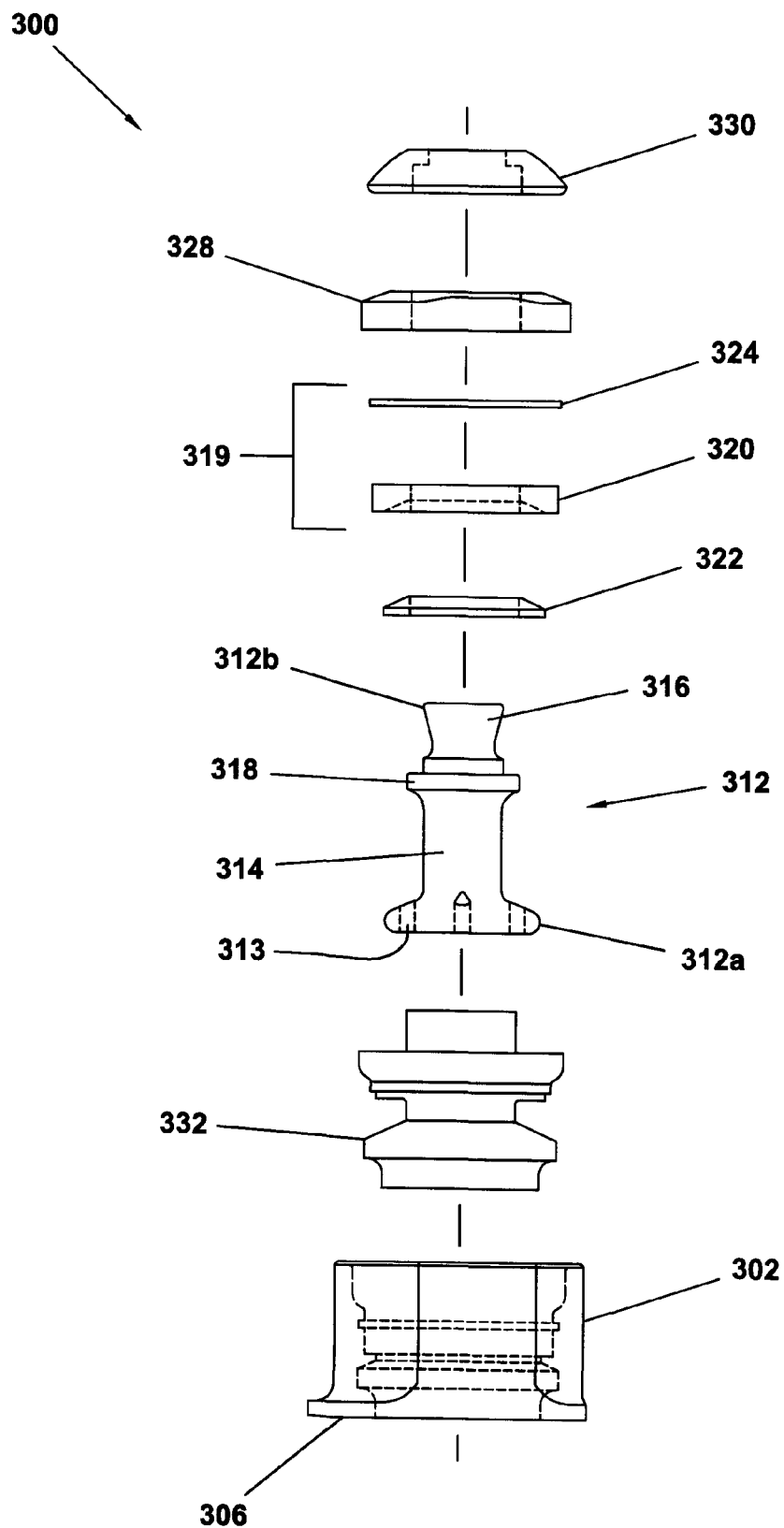
FIG. 43 is an exploded view of the multi-axis prosthetic ankle of FIG. 42.

As can best be observed in FIGS. 43 and 45, this embodiment of the lower leg connection component 312 has a distal end 312a that is generally flared outward. The distal end 312a of the lower leg connection component 312 may also be of another shape that assists with its retention in the receiving cavity 308. Preferably, but not necessarily, there are also one or more recesses or holes 313 in the flared distal end 312a of the lower leg connection component 312. These recesses or holes 313 receive elastomeric material during the molding process that assists with retention and/or helps to control movement of the of the lower leg connection component 312.

A shaft portion 314 extends upward from the distal end 312a, eventually terminating at the proximal end 312b in the pyramid adapter 316. The pyramid adapter 316 may be of a generally conventional design.

An outwardly protruding lip 318 may reside between the distal end 312a and the proximal end 312b of the prosthetic foot connection component 312. If present, the lip 318 may completely surround the shaft portion 314 or may extend only partially therearound. Preferably, such a lip 318 is also designed to engage an aperture present in a prosthetic dome 330 that may be used with the ankle 300.

The exemplary embodiment of the ankle 300 shown in FIGS. 42-46 typically includes several other components. Specifically, a retainer or retaining assembly is generally present within the receiving cavity to help prevent withdrawal of said lower leg connection component 312 therefrom. Such a retainer or retaining assembly may be of various design. For example, and as shown, such a retainer or retaining assembly 319 may comprise a separate element(s) that is installed into the receiving cavity 308 so as to engage the walls thereof. Alternatively, in certain embodiments, a retainer or retaining element may be formed directly in/by the walls of the receiving cavity 308. In any event, the lower leg connection component 312 is securely retained in the receiving cavity by the retainer.

In this particular embodiment of the ankle 300, the retaining assembly 319 includes a retaining washer 320 that engages the distal end 312a of the lower leg connection component 312 after installation into the receiving cavity 308. Preferably, but not necessarily, the interior of the retaining washer 320 is shaped alike or similar to the upper surface of the distal end 312a of the lower leg connection component 312. The retaining washer 320 has an aperture passing therethrough for allowing passage of a portion of the lower leg connection component 312. The retaining washer 320 remains within the prosthetic foot connection component 302 after assembly of ankle 300. The retaining 320 washer may be constructed from any of the materials described above as adequate for manufacturing the prosthetic foot connection component 302 or lower leg connection component 312, or may be manufactured from another suitable and, preferably rigid, material.

Although not essential to the present invention, an internal bearing 322 may also be provided and located between the retaining washer 320 and the distal end 312a of the lower leg connection component 312. If used, the shape of the internal bearing 322 preferably reflects the shape of the upper surface of the distal end 312a of the lower leg connection component 312 and the interior of the retaining washer 320. The internal bearing 322 has an aperture passing therethrough for allowing passage of a portion of the lower leg connection component 312. The internal bearing 322 may be comprised of various materials, but is preferably constructed of a low friction material.

In this embodiment of the retaining assembly 319, an internal snap ring 324 sits above the retaining washer 320 and seats in a receiving groove 326 located along the interior wall(s) of the receiving cavity 308. The snap ring 324 keeps at least the retaining washer 320 and internal bearing 322 properly located within the receiving cavity 308, thereby also assisting with retention of the lower leg connection component 312.

An external bearing 328 is preferably, but not necessarily, present. The external bearing 328 has an aperture passing therethrough for allowing passage of a portion of the lower leg connection component 312. As will be described in more detail below, the size and/or shape of the aperture can be adjusted to provide for different ranges of ankle motion. The external bearing 328 preferably resides atop a section of elastomeric material. The external bearing 328 also preferably resides at least partially within the receiving cavity 308 of the prosthetic foot connection component 302, although in other embodiments the external bearing may engage a top surface of the prosthetic foot connection component without entering the receiving cavity.

A prosthetic dome 330 may optionally be fitted over the proximal end 312b of the lower leg connection component 312 so that its underside rests atop or resides in close proximity to the top surface of the external bearing 328. Such a dome 330 is generally umbrella-shaped, and would be well known to one skilled in the art. The dome 330 has an aperture passing therethrough for allowing passage of at least the pyramid part 316 of the lower leg connection component 312. Preferably, the dome 330 is configured to receive and engage at least the lip portion 318 of the lower leg connection component 312. During flexion of the ankle the dome 330 moves along with the lower leg connection component 312, with at least a portion of its underside typically riding over top of the external bearing 328. In another embodiment, the dome 330 can be used without the external bearing 328, in which case the dome may rest atop the elastomeric material 332—which may be of a shape that conforms to the underside of the dome.

This particular embodiment of the ankle 300 is normally assembled by inserting the lower leg connection component 312, internal bearing 322, retaining washer 320, snap ring 324 and, optionally, the dome 330, into the receiving cavity 308 of the prosthetic foot connection component 302 such that the internal bearing is trapped between the lower leg connection component and the retaining washer and the snap ring enters the receiving groove 326. Placing the dome 330 in the mold prior to molding, while not necessary, may assist with controlling migration of the subsequently supplied elastomeric material.

This assembly of components is then placed into a special mold designed to receive the components and an amount of a subsequently supplied elastomeric material. The mold is typically designed to restrict the elastomeric material to a particular hardened size and/or shape, and/or to limit the elastomer to contact with only certain predetermined areas of the assembly (as is illustrated by the completed ankle assembly of FIG. 45). In particular, the mold may be designed to produce a column of elastomeric material that extends upward around the lower leg connection component 312 and is subsequently received by the aperture in the external bearing 328.

With the components held in position, an elastomeric material in a flowable state is injected or otherwise introduced into the mold and permitted to harden. The elastomeric material is preferably a rubber, and more preferably a thermoset rubber polymer having a high resistance and memory under cyclical loading. Non-limiting examples include butyl rubber, ethylene-propylene rubber, neoprene rubber, nitrile rubber, polybutadiene rubber, polyisoprene rubber, stereo rubber, styrene-butadiene rubber, natural rubber, or a combination of two or more of these rubbers. The use of other elastomeric materials is also possible.

The elastomeric material 332 thereby forms a casing around, and/or otherwise bonds to at least a portion of any components present and exposed within the receiving cavity 308. The elastomeric material 332 may also flow into the recesses or holes 313 in the prosthetic leg connection component, and the apertures of the retainer or retaining assembly 319 (such as the apertures in the internal bearing 322, retaining washer 320 and snap ring 324). A representative shape of molded elastomeric material 332 can be seen in FIGS. 43 and 45. Note that the elastomeric material 332 shape shown in FIG. 43 is intended to represent the elastic material as if removed intact from the prosthetic foot connection component after molding.

Once the above-described assembly and molding process is accomplished, the molded assembly is removed from the mold. The external bearing may then be installed over the protruding pyramid adapter 316 and inserted at least partially into the receiving cavity 308, where it floats on top of the hardened elastomeric material 332. The dome 330 is then finally installed over the top of the external bearing 328. In certain embodiments, the dome 330 may be retained on the ankle 300 by, for example, a press fit to the optional lip 318 of the lower leg connection component 312, or by an adhesive. In such an embodiment, the dome 330 is generally responsible for securing the position of the external bearing 328.

In another embodiment, the external bearing 328 may also be placed in the mold such that the elastomeric material 332 bonds thereto. For example, the elastomeric material 332 may be allowed to contact the underside of the external bearing 328 and to flow through the aperture present therein. In such a case, it may also be possible to contact and bond the elastomeric material to the dome 330.

Introducing the elastomeric material to the component assembly in the above-described manner allows the elastomeric material to provide a controlling resistance to plantar flexion, dorsi flexion, inversion, eversion, translation and internal/external rotational movement of a prosthetic foot to which the ankle 300 is attached. Resistance to such movement is provided by a corresponding compression of the elastomeric material. The compression resistance of the elastomeric material increases as the angle of ankle 300 pivot increases. When this resistance is equivalent to the turning (pivoting) load on the ankle 300, the elastomeric material may act as a fixed stop against further rotation. One skilled in the art can use data regarding the expected load on the ankle 300 and the compression resistance of the elastomeric material to optimize the design of the ankle.

The overall range of ankle articulation can also be controlled by manipulating the size of the space (gap) existing between the outside surface of the lower leg connection component 312 and the aperture in the external bearing 328. More particularly, a reduced gap results in less elastomeric material being present therebetween and, consequently, in a reduced range of motion. Conversely, an increased gap results in more elastomeric material being present therebetween and, an increased range of motion. The aperture in the external bearing 328 may be of virtually any shape, and may be of similar or dissimilar shape to the portion of the lower leg connection component 312 passing therethrough. The aperture may also be offset in order to limit certain types of motion (e.g., planar flexion, dorsi-flexion, inversion, eversion, etc.) and/or to increase others. Any combination of aperture size, shape and/or offset may be provided to control articulation in a desired manner. The shape of an appropriate portion of the lower leg connection component 312 may also be manipulated for this purpose, whether in conjunction with, or in lieu of, manipulation of the size, shape and/or offset of the aperture in the external bearing 328.

Figure 47:
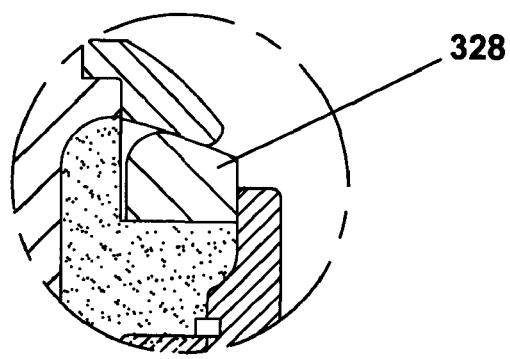
FIG. 47 is a detailed view of a section of a variation of the multi-axis prosthetic ankle shown in FIG. 42.
Figure 48:
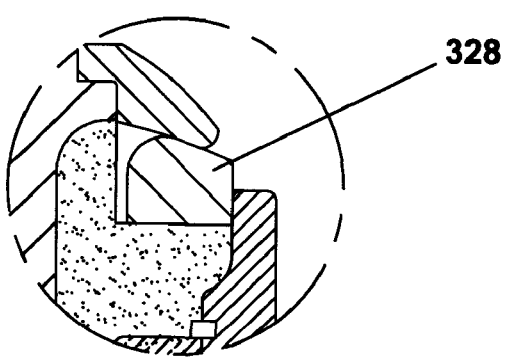
FIG. 48 is a detailed view of a section of another variation of the multi-axis prosthetic ankle shown in FIG. 42.
Figure 49:
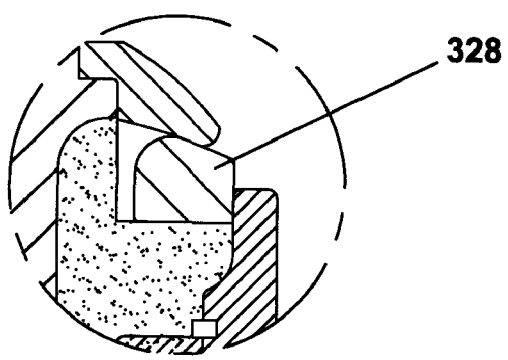
FIG. 49 is a detailed view of a section of yet another variation of the multi-axis prosthetic ankle shown in FIG. 42.

Specific variations of the prosthetic ankle 300 are represented in FIGS. 47-49. FIGS. 47-49 are detailed views of a portion of the ankle 300, wherein an alternate construction associated with the external bearing 328 can be seen.

In the specific embodiment of the ankle 300 shown in FIGS. 42-46 and described above, it is disclosed that the aperture in the external bearing 328 may be of different size and or shape to assist in controlling overall articulation of the ankle. However, in that disclosed embodiment, any gap resulting from a difference in size between the aperture and the outer surface of the lower leg connection component 312 is filled with elastomeric material. As a result, interchangeability of the external bearing 328 is substantially limited to one having an aperture of the same size and shape or, possibly, one having an increased aperture size (to fit over the elastomeric material). Therefore, while the range of motion of the ankle might possibly be increased by replacing the external bearing 328 with one having an aperture of increased size, the range of motion of the ankle cannot be reduced by replacing the external bearing with one having an aperture of decreased size. And, it has been determined that interchangeability of the external bearing 328 is desirable to provide the user thereof with the widest range of articulation adjustment.

As shown in detailed views A-C of FIGS. 47-49, a variation of the ankle 300 allows for the interchangeability of external bearings 328 having several different aperture sizes. That is, the ankle 300 is manufactured with an elastomeric section of some predetermined size and shape that allows for the installation of various external bearings 328 having several different aperture sizes. For example, the size of the elastomeric section may be selected so as to fit within the aperture of an external bearing 328 having the smallest aperture of a set of interchangeable external bearings. The smallest aperture may fit over the elastomeric section in mating contact, or a small gap may exist therebetween, such as is shown in FIG. 47. In this manner, external bearings 328 having smaller apertures may be interchanged with external bearings having larger apertures, such as those shown in FIGS. 48-49.

As can be understood from the foregoing description and from a review of FIGS. 47-49, employing external bearings 328 with increasingly larger apertures produces increasingly larger gaps between the aperture walls and the outer surface of the elastomeric material 332 (and lower leg connection component 312). This allows for greater motion of the lower leg connection component within the receiving cavity 308 of the prosthetic foot connection component 302 and, therefore, greater overall articulation of the ankle 300.

A prosthetic ankle 300 of such design allows a user maximum flexibility in choosing the amount of articulation of the ankle during use. For example, if a user wants less articulation, an external bearing 328 with a smaller aperture may be used. Contrarily, if a user wants more articulation, an external bearing with a larger aperture may be used. Articulation may be set to a desired limit based on everyday use, or different levels of articulation may be selected based on particular activities in which the user is engaged. As the external bearing 328 can be easily removed and replaced once the dome 330 is removed, adjustments to articulation of the ankle 300 can be quickly and frequently accomplished if desired.

To assist a user and or a prosthetist with setting overall ankle articulation, the external bearings 328 may be labeled or otherwise associated with some predetermined range of motion. A user or prosthetist may be able to obtain and employ a single external bearing 328 based on a desired range of ankle articulation or, alternatively, a set of external bearings may be provided with the ankle 300 or otherwise made available to allow for incremental adjustment of overall ankle articulation. The aperture of the external bearings 328 may have a shape and or size that limits it to use with only one or a few ankle variations. Alternatively, the external bearings 328 may be designed to be universally useable with any variation of the ankle 300.

While certain embodiments of the present invention are described in detail above, the scope of the invention is not to be considered limited by such disclosure, and modifications are possible without departing from the spirit of the invention as evidenced by the following claims:

What is claimed is:

1. A multi-axis prosthetic ankle having an adjustable range of articulation, comprising:
   a prosthetic foot connection component containing a receiving cavity;
   a lower leg connection component, at least a first end thereof installed into said receiving cavity;
   a retainer located in said receiving cavity for preventing upward displacement of said lower leg connection component with respect to said prosthetic foot connection component;
   an elastomeric material in said receiving cavity and substantially encasing any components present therein; and
   an interchangeable external bearing having an aperture through which a portion of said lower leg connection component passes, said external bearing residing atop a portion of said elastomeric material and at least partially within said receiving cavity;
   wherein overall articulation of said ankle is adjusted by exchanging one external bearing for another external bearing having an aperture of different size.

2. The multi-axis prosthetic ankle of claim 1, wherein said prosthetic foot connection component is a substantially hollow structure having rigid vertical walls.

3. The multi-axis prosthetic ankle of claim 1, wherein a second end of said lower leg connection component further includes a pyramid adapter, said pyramid adapter for connecting said ankle to a prosthetic leg.

4. The multi-axis prosthetic ankle of claim 1, wherein elastomeric material extends into said aperture in said external bearing.

5. The multi-axis prosthetic ankle of claim 1, further comprising a dome adapted for installation over said lower leg connection component and for movement over a top surface of said external bearing.

6. The multi-axis prosthetic ankle of claim 1, wherein a given external bearing is identifiable as providing some predefined range of ankle articulation.

7. The multi-axis prosthetic ankle of claim 1, further comprising a set of interchangeable external bearings for providing a range of different articulation limits.

8. The multi-axis prosthetic ankle of claim 1, wherein said aperture in each external bearing is of a specific shape that limits use of a given external bearing to one or a limited number of prosthetic ankles.

9. A multi-axis prosthetic ankle having an adjustable range of articulation, comprising:
   a prosthetic foot connection component containing a receiving cavity;
   a lower leg connection component having a distal end installed into said receiving cavity and adapted to facilitate retention therein, and a proximal end located outside said receiving cavity and adapted to connect said ankle to a prosthetic leg;
   a retainer located in said receiving cavity for preventing upward displacement of said lower leg connection component with respect to said prosthetic foot connection component;
   an elastomeric material residing within said receiving cavity and substantially encasing any components present therein;
   an interchangeable external bearing having an aperture through which an elastomerically covered portion of said lower leg connection component passes, said external bearing residing atop a portion of said elastomeric material and at least partially within said receiving cavity;

wherein overall articulation of said ankle is adjusted by exchanging one external bearing for another external bearing having an aperture of different size, the walls of said aperture in said external bearing acting as a hard stop against movement of said lower leg connection component.

10. The multi-axis prosthetic ankle of claim 9, wherein said prosthetic foot connection component is a substantially hollow structure having rigid vertical walls.

11. The multi-axis prosthetic ankle of claim 9, wherein a second end of said lower leg connection component further includes a pyramid adapter, said pyramid adapter for connecting said ankle to a prosthetic leg.

12. The multi-axis prosthetic ankle of claim 9, further comprising a dome adapted for installation over said lower leg connection component and for movement over a top surface of said external bearing.

13. The multi-axis prosthetic ankle of claim 9, wherein a given external bearing is identifiable as providing some predefined range of ankle articulation.

14. The multi-axis prosthetic ankle of claim 9, further comprising a set of interchangeable external bearings for providing a range of different articulation limits.

15. The multi-axis prosthetic ankle of claim 9, wherein said aperture in each external bearing is of a specific shape that limits use of a given external bearing to one or a limited number of prosthetic ankles.

16. A method of adjusting the overall range of articulation of a multi-axis prosthetic ankle having a lower leg connection component with at least a first end thereof installed into and retained in an elastomeric material-containing receiving cavity of a prosthetic foot connection component, comprising:

providing an interchangeable external bearing having an aperture through which a portion of said lower leg connection component passes;

locating said external bearing atop a portion of said elastomeric material and at least partially within said receiving cavity; and exchanging one external bearing for another external bearing having an aperture of different size, thereby altering the limits of possible movement of said lower leg connection component.

17. The method of claim 16, wherein the range of articulation is decreased by exchanging an installed external bearing for an external bearing having an aperture of decreased size.

18. The method of claim 16, wherein the range of articulation is increased by exchanging an installed external bearing for an external bearing having an aperture of increased size.

19. The method of claim 16, further comprising identifying a given external bearing as providing a particular range of articulation when installed to said ankle.

20. The method of claim 16, wherein said portion of said lower leg connection component that passes through said aperture in said external bearing is at least partially encased in elastomeric material.

* * * * *

UNITED STATES PATENT AND TRADEMARK OFFICE
CERTIFICATE OF CORRECTION

| | | |
|---|---|---|
| PATENT NO. | : 7,833,287 B2 | Page 1 of 1 |
| APPLICATION NO. | : 11/613843 | |
| DATED | : November 16, 2010 | |
| INVENTOR(S) | : Jeffrey L. Doddroe et al. | |

It is certified that error appears in the above-identified patent and that said Letters Patent is hereby corrected as shown below:

In Column 11, line 58, please delete "360" and insert -- 36°--

In Column 15, line 34, please delete "100" and insert -- 10° --

In Column 18, line 62, please delete "100" and insert -- 10° --

In Column 25, line 6, please delete "bearing having an aperture of different size, the walls of" and insert -- bearing having an aperture of different size, walls of --

Signed and Sealed this
First Day of March, 2011

David J. Kappos
*Director of the United States Patent and Trademark Office*